US008911557B2

(12) United States Patent
Nguyen et al.

(10) Patent No.: US 8,911,557 B2
(45) Date of Patent: *Dec. 16, 2014

(54) METHOD AND APPARATUS FOR CONVEYING A CELLULOSIC FEEDSTOCK

(75) Inventors: Quang A. Nguyen, Chesterfield, MO (US); Sunalie N. Hillier, Georgetown (CA); Murray J. Burke, Oakville (CA)

(73) Assignee: Abengoa Bioenergy New Technologies, LLC., Chesterfield, MO (US)

( * ) Notice: Subject to any disclaimer, the term of this patent is extended or adjusted under 35 U.S.C. 154(b) by 1039 days.

This patent is subject to a terminal disclaimer.

(21) Appl. No.: 12/181,724

(22) Filed: Jul. 29, 2008

(65) Prior Publication Data

US 2010/0024809 A1 Feb. 4, 2010

(30) Foreign Application Priority Data

Jul. 24, 2008 (CA) ..................................... 2638157

(51) Int. Cl.
*C13K 1/02* (2006.01)
*C12M 1/26* (2006.01)
*C12M 1/00* (2006.01)

(52) U.S. Cl.
CPC .................. *C13K 1/02* (2013.01); *C12M 33/16* (2013.01); *C12M 45/20* (2013.01); *Y02E 50/16* (2013.01); *C12M 45/09* (2013.01)
USPC ................. 127/37; 127/1; 366/145; 366/147; 366/149; 366/153.3; 366/167.1

(58) Field of Classification Search
CPC ...... C12M 45/03; C12M 45/06; C12M 45/20; C12M 33/16; C12M 45/09; C13K 1/02; C13K 13/00; B01F 3/20; B01F 5/00; Y02E 50/16

USPC .................. 34/329, 343, 357, 363; 127/1, 37; 198/657; 366/147, 149, 153.3, 167.1, 366/145; 406/53, 55

See application file for complete search history.

(56) References Cited

U.S. PATENT DOCUMENTS 319,299 A 6/1885 Morgan
459,113 A 9/1891 Rymal (Continued)

FOREIGN PATENT DOCUMENTS

CA 1070537 1/1980
CA 1096374 B 2/1981

(Continued)

OTHER PUBLICATIONS

Q.A. Nguyen et al., "NREL/DOE Ethanol Pilot-Plant: Current Status and Capabilities" (1996) 58 Bioresource Technology 189.

(Continued)

*Primary Examiner* — David A Reifsnyder
(74) *Attorney, Agent, or Firm* — Armstrong Teasdale LLP

(57) ABSTRACT

A method and apparatus for preparing a cellulosic feedstock are disclosed. Embodiments of the method comprise passing the cellulosic feedstock through an optional impregnation chamber to an outlet of the impregnation chamber, passing the cellulosic feedstock from the outlet of the impregnation chamber to a holding tank having an inlet and an outlet, and conveying the cellulosic feedstock downwardly and laterally as it travels through the holding tank. Embodiments of the apparatus comprise at least one sidewall defining a passage. The passage has an upper portion and a lower portion, and the lower portion has a greater cross-sectional area than the upper portion. At least one inlet is provided adjacent the upper portion, and at least one outlet is provided adjacent the lower portion, at an elevation below the inlet.

9 Claims, 10 Drawing Sheets

(56) References Cited

U.S. PATENT DOCUMENTS

| | | |
|---|---|---|
| 1,073,425 A | 9/1913 | Lambert |
| 1,106,736 A | 8/1914 | Schuller |
| 1,173,825 A | 2/1916 | McWallen |
| 1,190,923 A | 7/1916 | Lindquist |
| 1,247,153 A | 11/1917 | Roberts |
| 1,560,855 A | 11/1925 | Queneau |
| 1,824,221 A | 9/1931 | Mason |
| 2,080,327 A | 5/1937 | McKinnis |
| 2,086,701 A | 7/1937 | Dreyfus |
| 2,263,608 A | 11/1941 | Brown |
| 2,333,739 A | 11/1943 | Puckett |
| 2,541,058 A | 2/1951 | Heritage et al. |
| 2,541,059 A | 2/1951 | Heritage et al. |
| 2,541,127 A | 2/1951 | Van Beckum |
| 2,570,042 A | 10/1951 | West |
| 2,595,827 A | 5/1952 | Boruff et al. |
| 2,615,883 A | 10/1952 | Sweeney et al. |
| 2,697,703 A | 12/1954 | Heritage et al. |
| 2,758,031 A * | 8/1956 | Ozai-Durrani ................ 426/461 |
| 3,017,404 A | 1/1962 | Ball |
| 3,109,560 A | 11/1963 | Rosenleaf |
| 3,199,731 A | 8/1965 | Brauer et al. |
| 3,223,697 A | 12/1965 | Ball et al. |
| 3,357,437 A | 12/1967 | Maguire |
| 3,383,277 A | 5/1968 | Gordon et al. |
| 3,407,943 A | 10/1968 | Douglass, Jr. |
| 3,572,593 A | 3/1971 | Guarisco |
| 3,617,433 A | 11/1971 | Sutherland |
| 3,640,509 A | 2/1972 | Inamura et al. |
| 3,743,572 A | 7/1973 | Richter et al. |
| 3,817,826 A | 6/1974 | Hoye |
| 3,964,874 A | 6/1976 | Maruko et al. |
| 3,964,880 A | 6/1976 | Siegrist |
| 4,023,982 A | 5/1977 | Knauth |
| 4,055,673 A | 10/1977 | Mueller et al. |
| 4,062,304 A | 12/1977 | Herbold et al. |
| 4,119,025 A | 10/1978 | Brown |
| 4,136,207 A | 1/1979 | Bender |
| 4,160,695 A | 7/1979 | Dietrichs et al. |
| 4,181,796 A | 1/1980 | Dietrichs et al. |
| 4,186,658 A | 2/1980 | Brown |
| 4,196,827 A | 4/1980 | Leafdale |
| 4,200,692 A | 4/1980 | Puls et al. |
| 4,211,163 A | 7/1980 | Brown et al. |
| 4,237,226 A | 12/1980 | Grethlein |
| 4,281,934 A | 8/1981 | Krause |
| 4,286,884 A | 9/1981 | Retrum |
| 4,296,864 A | 10/1981 | Misaka et al. |
| 4,316,748 A | 2/1982 | Rugg et al. |
| 4,331,447 A | 5/1982 | Kamada et al. |
| 4,341,353 A | 7/1982 | Hamilton et al. |
| 4,364,667 A | 12/1982 | Reiner |
| 4,412,485 A | 11/1983 | Brown |
| 4,427,453 A | 1/1984 | Reitter |
| 4,432,805 A | 2/1984 | Nuuttila et al. |
| 4,436,586 A | 3/1984 | Elmore |
| 4,451,567 A | 5/1984 | Ishibashi et al. |
| 4,461,648 A | 7/1984 | Foody |
| 4,470,851 A | 9/1984 | Paszner et al. |
| 4,483,625 A | 11/1984 | Fisher et al. |
| 4,511,433 A | 4/1985 | Tournier et al. |
| 4,584,057 A | 4/1986 | Rowe et al. |
| 4,600,590 A | 7/1986 | Dale |
| 4,615,742 A | 10/1986 | Wright |
| 4,645,541 A | 2/1987 | Delong |
| 4,667,373 A | 5/1987 | Roder |
| 4,670,944 A | 6/1987 | Thrash |
| 4,676,363 A | 6/1987 | Buchmuller et al. |
| 4,746,404 A | 5/1988 | Laakso |
| 4,751,034 A | 6/1988 | Delong et al. |
| 4,752,579 A | 6/1988 | Arena et al. |
| 4,764,596 A | 8/1988 | Lora et al. |
| 4,775,239 A | 10/1988 | Martinek et al. |
| 4,798,651 A | 1/1989 | Kokta |
| 4,867,846 A | 9/1989 | Fleck |
| 4,869,786 A | 9/1989 | Hanke |
| 4,908,098 A | 3/1990 | Delong et al. |
| 4,908,099 A | 3/1990 | Delong |
| 4,911,558 A | 3/1990 | Teske |
| 4,947,743 A | 8/1990 | Brown et al. |
| 4,966,650 A | 10/1990 | Delong et al. |
| 4,997,488 A | 3/1991 | Gould et al. |
| 5,012,731 A | 5/1991 | Maisonneuve |
| 5,023,097 A | 6/1991 | Tyson et al. |
| 5,034,099 A | 7/1991 | Nilsson |
| 5,047,332 A | 9/1991 | Chahal |
| 5,052,874 A | 10/1991 | Johanson |
| 5,100,066 A | 3/1992 | Frei |
| 5,114,488 A | 5/1992 | Huber et al. |
| 5,122,228 A | 6/1992 | Bouchette et al. |
| 5,135,861 A | 8/1992 | Pavilon |
| 5,176,295 A | 1/1993 | Stefanik |
| 5,181,804 A | 1/1993 | Wysong et al. |
| 5,188,298 A | 2/1993 | Gerber |
| 5,198,074 A | 3/1993 | Villavicencio et al. |
| 5,221,357 A | 6/1993 | Brink |
| 5,338,366 A | 8/1994 | Grace et al. |
| 5,348,871 A | 9/1994 | Scott et al. |
| 5,366,558 A | 11/1994 | Brink |
| 5,411,594 A | 5/1995 | Brelsford |
| 5,417,492 A | 5/1995 | Christian et al. |
| 5,424,417 A | 6/1995 | Torget et al. |
| 5,487,989 A | 1/1996 | Fowler et al. |
| 5,503,996 A | 4/1996 | Torget et al. |
| 5,504,259 A | 4/1996 | Diebold et al. |
| 5,536,325 A | 7/1996 | Brink |
| 5,571,703 A | 11/1996 | Chieffalo et al. |
| 5,597,714 A | 1/1997 | Farone et al. |
| 5,611,930 A | 3/1997 | Nguyen et al. |
| 5,628,830 A | 5/1997 | Brink |
| 5,677,154 A | 10/1997 | Van Draanen et al. |
| 5,705,216 A | 1/1998 | Tyson |
| 5,705,369 A | 1/1998 | Torget et al. |
| 5,730,837 A | 3/1998 | Black et al. |
| 5,733,758 A | 3/1998 | Nguyen |
| 5,735,916 A | 4/1998 | Lucas et al. |
| 5,791,779 A | 8/1998 | Smith |
| 5,843,760 A | 12/1998 | Zhang et al. |
| 5,863,389 A | 1/1999 | White et al. |
| 5,916,780 A | 6/1999 | Foody et al. |
| 5,932,452 A | 8/1999 | Mustranta et al. |
| 6,022,419 A | 2/2000 | Torget et al. |
| 6,063,204 A | 5/2000 | Hester et al. |
| 6,090,595 A | 7/2000 | Foody et al. |
| 6,199,299 B1 | 3/2001 | Prough et al. |
| 6,228,177 B1 | 5/2001 | Torget |
| 6,330,767 B1 | 12/2001 | Carr et al. |
| 6,336,573 B1 | 1/2002 | Johanson |
| 6,409,841 B1 | 6/2002 | Lombard |
| 6,419,788 B1 | 7/2002 | Wingerson |
| 6,423,145 B1 | 7/2002 | Nguyen et al. |
| 6,498,029 B2 | 12/2002 | Keller, Jr. et al. |
| 6,557,267 B2 | 5/2003 | Wanger |
| 6,569,653 B1 | 5/2003 | Alard et al. |
| 6,572,734 B2 | 6/2003 | Baker |
| 6,620,292 B2 | 9/2003 | Wingerson |
| 6,648,251 B1 | 11/2003 | Chollet |
| 6,660,506 B2 | 12/2003 | Nguyen et al. |
| 6,737,258 B2 | 5/2004 | Hames et al. |
| 6,743,928 B1 | 6/2004 | Zeitsch |
| 6,908,995 B2 | 6/2005 | Blount |
| 6,927,048 B2 | 8/2005 | Verser et al. |
| 7,109,005 B2 | 9/2006 | Eroma et al. |
| 7,178,698 B2 | 2/2007 | Forslund et al. |
| 7,198,925 B2 | 4/2007 | Foody |
| 7,238,242 B2 | 7/2007 | Pinatti et al. |
| 7,396,434 B2 | 7/2008 | Rodriguez Rivera et al. |
| 7,445,691 B2 | 11/2008 | Snekkenes et al. |
| 7,461,591 B2 | 12/2008 | Babbini |
| 7,494,675 B2 | 2/2009 | Abbas et al. |
| 7,503,981 B2 | 3/2009 | Wyman et al. |
| 7,875,444 B2 | 1/2011 | Yang et al. |
| 7,901,511 B2 | 3/2011 | Griffin et al. |
| 7,937,851 B2 * | 5/2011 | Rajagopalan et al. .......... 34/357 |

(56) References Cited

U.S. PATENT DOCUMENTS

| | | |
|---|---|---|
| 7,993,463 B2 | 8/2011 | Griffin et al. |
| 8,051,986 B2 | 11/2011 | Lees |
| 8,053,566 B2 | 11/2011 | Belanger et al. |
| 8,193,395 B2 | 6/2012 | Fenton et al. |
| 8,449,680 B2 | 5/2013 | Burke et al. |
| 2002/0003032 A1 | 1/2002 | Nay et al. |
| 2002/0164731 A1 | 11/2002 | Eroma et al. |
| 2003/0089465 A1 | 5/2003 | Schaible et al. |
| 2004/0121436 A1 | 6/2004 | Blount |
| 2004/0154760 A1 | 8/2004 | Dean |
| 2004/0171136 A1 | 9/2004 | Holtzapple et al. |
| 2004/0231661 A1 | 11/2004 | Griffin et al. |
| 2004/0231811 A1 | 11/2004 | Engstrand et al. |
| 2005/0269048 A1 | 12/2005 | Rodriguez et al. |
| 2006/0088922 A1 | 4/2006 | Yang et al. |
| 2006/0163118 A1 | 7/2006 | Kelsey et al. |
| 2006/0169430 A1 | 8/2006 | Tarasenko |
| 2006/0188965 A1 | 8/2006 | Wyman et al. |
| 2006/0233864 A1 | 10/2006 | Power |
| 2006/0272518 A1 | 12/2006 | Babbini |
| 2006/0275895 A1 | 12/2006 | Jensen et al. |
| 2007/0037267 A1 | 2/2007 | Lewis et al. |
| 2007/0148751 A1 | 6/2007 | Griffin et al. |
| 2007/0209974 A1 | 9/2007 | Lees |
| 2007/0215300 A1 | 9/2007 | Upfal et al. |
| 2007/0218530 A1 | 9/2007 | Duck et al. |
| 2007/0227063 A1 | 10/2007 | Dale et al. |
| 2008/0026431 A1 | 1/2008 | Saito et al. |
| 2008/0038784 A1 | 2/2008 | D'Arnaud-Taylor |
| 2008/0227161 A1 | 9/2008 | Levie et al. |
| 2009/0029432 A1 | 1/2009 | Abbas et al. |
| 2009/0062516 A1 | 3/2009 | Belanger et al. |
| 2009/0069550 A1 | 3/2009 | Belanger et al. |
| 2009/0098616 A1 | 4/2009 | Burke et al. |
| 2009/0098617 A1 | 4/2009 | Burke et al. |
| 2009/0240088 A1 | 9/2009 | Fenton et al. |
| 2009/0246848 A1 | 10/2009 | Noel |
| 2010/0024806 A1* | 2/2010 | Burke et al. ............... 127/1 |
| 2010/0024807 A1* | 2/2010 | Burke et al. ............... 127/1 |
| 2010/0024808 A1* | 2/2010 | Burke et al. ............... 127/1 |
| 2010/0024809 A1 | 2/2010 | Burke et al. |
| 2010/0028089 A1* | 2/2010 | Burke et al. ............. 406/53 |
| 2010/0124583 A1 | 5/2010 | Medoff |
| 2010/0186735 A1* | 7/2010 | Burke et al. ............... 127/1 |
| 2010/0186736 A1* | 7/2010 | Burke et al. ............... 127/1 |
| 2011/0011391 A1* | 1/2011 | Burke ....................... 127/1 |
| 2012/0111321 A1* | 5/2012 | Nguyen et al. ............. 127/1 |

FOREIGN PATENT DOCUMENTS

| | | |
|---|---|---|
| CA | 1147105 A | 5/1983 |
| CA | 1173825 A1 | 9/1984 |
| CA | 1190923 A1 | 7/1985 |
| CA | 1267407 | 3/1990 |
| CA | 1287705 | 8/1991 |
| CA | 2037275 A1 | 8/1992 |
| CA | 1322366 C | 9/1993 |
| CA | 2063547 A1 | 9/1993 |
| CA | 2065939 A1 | 10/1993 |
| CA | 2339002 A1 | 7/1999 |
| CA | 2638150 A1 | 1/2010 |
| CA | 2638159 | 1/2010 |
| CN | 200981760 | 11/2007 |
| EP | 0487793 A1 | 6/1992 |
| EP | 1036236 | 9/1998 |
| EP | 0884391 B1 | 1/2002 |
| EP | 1316620 A2 | 6/2003 |
| FR | 777824 | 3/1935 |
| GB | 892506 | 3/1957 |
| GB | 1043460 A | 9/1966 |
| WO | 9213849 A1 | 8/1992 |
| WO | 9640970 A1 | 12/1996 |
| WO | 9732073 A1 | 9/1997 |
| WO | 0238787 A2 | 5/2002 |
| WO | 2004018645 A2 | 3/2004 |
| WO | 2004081193 A2 | 9/2004 |
| WO | 2004106624 A1 | 12/2004 |
| WO | 2005079190 A2 | 9/2005 |
| WO | 2005118165 A1 | 12/2005 |
| WO | 2006017655 A3 | 2/2006 |
| WO | 2006034591 A1 | 4/2006 |
| WO | 2006055362 A1 | 5/2006 |
| WO | 2006-063467 | 6/2006 |
| WO | 2007009463 A2 | 1/2007 |
| WO | 2007065241 A1 | 6/2007 |
| WO | WO 2007064296 A1 * | 6/2007 |
| WO | 2007111605 A1 | 10/2007 |
| WO | 2008086115 A2 | 7/2008 |
| WO | 2008144903 A1 | 12/2008 |
| WO | 2009012779 | 1/2009 |
| WO | 2009018469 A1 | 2/2009 |
| WO | 2009089439 A1 | 7/2009 |
| WO | 2010006840 A2 | 1/2010 |
| WO | 2010009547 A1 | 1/2010 |
| WO | 2010009548 A1 | 1/2010 |
| WO | 2010009550 A1 | 1/2010 |
| WO | 2010009551 | 1/2010 |
| WO | WO 2010009549 A1 * | 1/2010 |
| WO | 2010083600 A1 | 7/2010 |
| WO | 2010083601 A1 | 7/2010 |
| WO | 2011028554 A1 | 3/2011 |

OTHER PUBLICATIONS

R.P. Overend & E. Chornet, "Fractionation of lignocellulosics by steam-aqueous pretreatments" (1987) 321 Phil. Trans. R. Soc. Lond. A. 523.

D. Ballerini et al., "Ethanol Production from Lignocellulosics: Large Scale Experimentation and Economics" (1994) 50 Biousource Technology 17.

K.M.F. Kazi, P. Jollez, & E. Chornet, "Preimpregnation: An Important Step for Biomass Refining Processes" (1998) 15:2 Biomass and Bioenergy 125.

M.P. Tucker et al., "Comparison of Yellow Poplar Pretreatment Between NREL Digester and Sunds Hydrolyzer" (1998) 70-72 Applied Biochemistry and Biotechnology 25.

Charles E. Wyman et al., "Comparative Sugar Recovery Data from Laboratory Scale Application of Leading Pretreatment Technologies to Corn Stover" (2005) 96 Bioresource Technology 2026.

Charles E. Wyman et al., "Coordinated Development of Leading Biomass Pretreatment Technologies" (2005) 96 Bioresource Technology 1959.

Nathan Mosier et al., "Features of Promising Technologies for Pretreatment of Lignocellulosic Biomass" (2005) 96 Biosource Technology 673.

Tim Eggeman & Richard T. Elander, "Process and Economics Analysis of Pretreatment Technologies" (2005) 96 Bioresource Technology 2019.

Abengoa Bioenergy, Press Release, "Abengoa Bionergy Awarded DOE Financial Assistance Agreement" (Feb. 28, 2007), online: Abongoa Bioenergy <http://www.abengoabioenergy.es/corp/web/en/acerca_de/sala_de_prensa/historico/2007/20070228_noticias.html#>.

Outputs from the EPOBIO Workshop, Greece, "Products from Plants—From Crops and Forests to Zero Waste Biorefineries" (May 15-17, 2007).

Abengoa Bioenergy, Press Release, "Abengoa Bionergy Opens Pilot Plant for the Energy of the Future" (Oct. 15, 2007), online: Abengoa Bioenergy <http://www.abengoabioenergy.es/corp/web/en/acerca_de/sala_de_prensa/historico/2007/20071015_noticias.html#>.

Merrick & Company, Final Report of Jun. 14, 1999, "Softwood Biomass to Ethanol Feasibility Study" (Aug. 2004) Subcontractor Report published by National Renewable Energy Laboratory.

Merrick & Company, Final Report of Jan. 2000, "Building a Bridge to the Corn Ethanol Industry. Corn Stover to Ethanol at High Plains Corporation's York, Nebraska Co-Located Plant Site."

Melvin P. Tucker et al., "Conversion of Distiller's Grain into Fuel Alcohol and a Higher-Value Animal Feed by Dilute-Acid Pretreament" (2004) 113-116 Applied Biochemistry and Biotechnology 1139.

(56) References Cited

OTHER PUBLICATIONS

Melvin P. Tucker et al., "Effects of Temperature and Moisture on Dilute-Acid Steam Explosion Pretreatment of Corn Stover and Cellulase Enzyme Digestibility" (2003) 105-108 Applied Biochemistry and Biotechnology 165.

Kyoung Heon Kim et al., "Continuous Countercurrent Extraction of Hemicellulose from Pretreated Wood Residues" (2001) 91-93 Applied Biochemistry and Biotechnology 253.

Quang A. Nguyen et al., "Two-Stage Diute-Acid Pretreatment of Softwoods" (2000) 84-86 Applied Biochemistry and Biotechnology 561.

Daniel J. Schell et al., "Dilute-Sulfuric Acid Pretreatment of Corn Stover in Pilot-Scale Reactor" (2003) 105-108 Applied Biochemistry and Biotechnology 69.

Q.A. Nguyen & J.N. Saddler, "An Integrated Model for the Technical and Economic Evaluation of an Enzymatic Biomass Conversion Process" (1991) 35 Bioresource and Technology 275.

Q.A. Nguyen et al., "Dilute Acid Pretreatment of Softwoods", Scientific Note, (1998) 70-72 Applied Biochemistry and Biotechnology 77.

Q.A. Nguyen et al., "Dilute Acid Hydrolysis of Softwoods", Scientific Note, (1999) 77-79 Applied Biochemistry and Biotechnology 133.

Raphael Katzen & Donald F. Othmer, "Wood Hydrolysis. A Continuous Process" (1942) 34 Industrial and Engineering Chemistry 314.

"Transactions of the Institution of Chemical Engineers" (1993) 11 Institution of Chemical Engineers, London, the United Kingdom.

Diane Knappert, Hans Grethlein & Alvin Converse, "Partial Acid Hydrolysis of Cellulosic Materials as a Pretreatment for Enzymatic Hydrolysis" (1980) 22 Biotechnology and Bioengineering 1449.

Sung Bae Kim & Y.Y. Lee, "Diffusion of Sulfuric Acid within Lignocellulosic Biomass Particles and its Impact on Dilute-Acid Pretreatment" (2002) 83 Bioresource Technology 165.

Alan W. Roberts, "Design Considerations and Performance Evaluation of Screw Conveyors", online: The South African Institute of Materials Handling <http://www.saimh.co.za/beltcon/beltcon11/beltcon1114.htm>.

National Renewable Energy Laboratory, "Process Design and Cost Estimate of Critical Equipment in the Biomass to Ethanol Process. Acid Hydrolysis Reactors Batch Systems", Report (Seattle, Washington: Harris Group Inc., 2001).

Osamu Kitani & Carl W.. Hall, eds., "Biomass Handbook" 470-474 (Gordon and Breach Science Publishers: New York).

Buell Classifier Fisher-Klosterman, Leaflet, "Operation Principles and Efficiency".

Process Sensors Corporation, "On-Line Moisture Measurement and Control Manufacturing Industries Worldwide", Product Information, online: Process Sensors Corporation <http://processsensors.com/index.html?gclid=CKT27fXvJ0CFREWagodclkUcw>.

Roger M. Rowell, Raymond A. Young, & Judith K. Rowell, eds., Paper and Composites from Agro-Based Resources (Lewis Publishers).

G.H.Emert et al., "Gasohol/Biomass Developments: Economic Update of the Gulf Cellulose Alcohol Process" (Sep. 1980) Chemical Engineering Progress 47.

Ron Kotrba, "The Project of a Lifetime" (Feb. 2006), Ethanol Producer Magazine.

National Renewable Energy Laboratory, "Research Advances: NREL Leads the Way. Cellulosic Ethanol", Brochure, (Mar. 2007), online: National Renewable Energy Laboratory <http://www.nrel.gov/biomass/pdfs/40742.pdf>.

National Renewable Energy Laboratory, Fact Sheet, "Clean Cities: Ethanol Basics" (Oct. 2008), online: U.S. Department of Energy <www.afdc.energy.gov/afdc/pdfs/43835.pdf>.

Brent D. Yacobucci, "Fuel Ethanol: Background and Public Policy Issues", (Mar. 3, 2006), CRS Report for Congress, online: U.S. Department of State, Foreign Press Centre <fpc.state.gov/documents/organization/62837.pdf>.

U.S. Department of Energy, Energy Efficiency & Renewable Energy, Alternative Fuels & Advanced Vehicles Data Center, Article, "Ethanol Market Penetration", online: U.S Department of Energy <http://www.afdc.energy.gov/afdc/ethanol/market.html>.

Kenneth W.Britt, ed., "Handbook of Pulp and Paper Technology", 2nd. ed. (New York: Van Nostrand Reinhold Company).

A. Aden et al., "Lignocellulosic Biomass to Ethanol Process Design and Economics Utilizing Co-Current Dilute Acid Prehydrolysis and Enzymatic Hydrolysis for Corn Stover", (Jun. 2002), Technical Report published by National Renewable Energy Laboratory.

U.S. Department of Energy Office of Science, Genomics Science Program, "Fuel Ethanol Production", online: U.S. Department of Energy Office of Science <http://genomicscience.energy.gov/biofuels/ethanolproduction.shtml>.

Metso Automation, Matso Automation's Newsletter for Neles and Jamesbury products, "Biofuels—a growth market for Metso", (Summer 2008), online: Metso <http://valveproducts.metso.com/metsoautomation/DocDB/catalogs/catalog.taf?pg_parent=397>.

SunOpta Inc., News Release, "SunOpta Announces Sale of Cellulosic Ethanol Facility to China Resources Alcohol Corporation", (Jun. 23, 2006), online: SunOpta Inc. <http://investor.sunopta.com/releasedetail.cfm?ReleaseID=287111>.

Ralph P. Overend, Slideshow, "The Lignocellulosic bottleneck: material properties, architecture and pretreatment".

Robert Wooley et al., "Lignocellulosic Biomass to Ethanol Process Design and Economics Utilizing Co-Current Dilute Acid Prehydrolysis and Enzymatic Hydrolysis Current and Futuristic Scenarios", (Jul. 1999), National Renewable Energy Laborator. Technical Report.

Nathan S. Masier, "Cellulosic Ethanol—Biofuel Beyond Corn" Bio Energy, Purdue University.

U.S Securities and Exchange Commission, "Annual Report Under Section 13 or 15(d) of the Securities Exchange Act of 1934", for Bluefire Ethanol Fuels, Inc. Signed on Feb. 28, 2008.

U.S Securities and Exchange Commission, "Annual Report Under Section 1 or (15)d of the Securities Exchange Act of 1934", for CleanTech Biofuels, Inc. Signed on Mar. 28, 2008.

Brownell et al., "Steam-Explosion Pretreatment of Wood: Effect of Chip Size, Acid, Moisture Content and Pressure Drop", Biotechnology and Bioengineering, vol. 28 pp. 792-801 (1986).

International Search Report and the Written Opinion received on the corresponding PCT Application No. PCT/CA2009/001036, dated Nov. 13, 2009.

International Search Report received on the corresponding PCT application No. PCT/CA2010/000088, mailed as a corrected version on Jun. 17, 2010.

International Search Report received in connection to the co-pending International patent application No. PCT/CA2010/000087, mailed on May 4, 2010.

Duff et al., "Bioconversion of forest products industry waste cellulosics to fuel ethanol: A review", Bioresource Technology, vol. 5 pp. 1-33 (1996).

International Search Report received in connection to the co-pending international patent application No. PCT/CA2010/000088, mailed on May 14, 2010.

Cullis et al. Effect of Initial Moisture Content and Chip Size on the Bioconversion Efficiency of Softwood Lignocellulosics; Biotechnology and Bioengineering, vol. 85, No. 4, pp. 413-421, (2004).

International Search Report received on the corresponding International Application No. PCT/CA2009/001034, mailed on Oct. 20, 2009.

International Preliminary Report on Patentability received on the corresponding International Application No. PCT/CA2009/001034, issued on Jan. 25, 2011.

*Abengoa Bioenergy New Technologies Inc. f/k/a Abengoa Bioenergy R&D, Inc. v. Mascoma Corporation*; Notice of Arbitration and Statement of Claim, submitted to American Arbitration Association Commercial Arbitration Tribunal on Nov. 2, 2011.

International Search Report received in connection to the co-penging International patent application No. PCT/CA2010/000087, mailed on May 4, 2010.

Cullis et al. Effect of intial Moisture Content and Chip Size on the Bioconversion Efficiency of Softwood Lignocellulosics; Biotechnology and Bioengineering, vol. 85, No. 4, pp. 413-421, (2004).

(56) References Cited

OTHER PUBLICATIONS

"Biofuels Pilot Plant Under Way," Newsbriefs, Chemical Week, Oct. 13-20, 2008, p. 4.
"Easy Steps for Optimal Yeast Rehydration," Laboratory Protocol, Scott Laboratories, Petaluma CA, 1 page.
"Enzyme Sugar-Ethanol Platform Project," NREL, U.S. Dept. of Energy by Midwest Research Institute, Battelle, Bechtel, 47 pages.
"Ethanol Annual Report FY 1990", SERI, TP-231/3996, Prepared for the U.S. DOE, Jan. 1991, Contract No. DE-ACO2-83CH10093, Texeira, R.H. and Goodman, B.J., editors, 344 pages.
"Lessons Learned from Existing Biomass Power Plants," Feb. 2000, NREL/SR-570-26946, G. Wiltsee, Appel Consultants, Inc., Valencia, CA, 149 pages.
"Process Design and Cost Estimate of Critical Equipment in the Biomass to Ethanol Process," Subcontract ACO-9-29067-01, Acid Hydrolysis Reactors Batch System, Report 99-10600/18, NREL, (Prepared by Harris Group Inc., Seattle, Washington, 2001), 36 pages.
"Types of Lignin and Their Properties," 2001, Information Service from the Lignin Institute, 9/1:4 pages, www.lignin.org/01augdialogue.html.
Abstract of Chinese Patent Application CN 101310879 A, 2008, Institute of Process Engineering, Chinese Academy of Sciences.
Activator 90, Product Brochure, 2009, Loveland Products Inc., No. 6566_05/09, 1 page.
Al-Ahalay, A.S.M., "A Study of Some Anatomical Chemical Properties and Specific Gravity of Casuarina Equisetifolia Forst. Wood Grown in Iraq." 1985, AGRIS Record No. IQ8500239, Abstract, 1 page.
AMISTCO Tower Trays, Product Brochure, Amistco Separation Products, Inc., 8 pages.
Antongiovanni, M., et al., "Variability in Chemical Composition of Straws," 1991, CIHEAM—Options Mediterraneennes, Serie Seminaires, 16:49-53.
Awafo, V.A., et al., "Evaluation of Combination Treatments of Sodium Hydroxide and Steam Explosion for the Production of Cellulase—Systems by Two T. reesei Mutants Under Solid—State Fermentation Conditions," 2000, Bioresource Tech, 73:235-245.
Azadbakht, M., et al., "Preparation of Lignin From Wood Dust as Vanillin Source and Comparison of Different Extraction Methods," Oct. 2004, Int J of Biol and Biotech, 1/4:535-537, Abstract Only, 1 page.
Bakker, R. R.e et al., "Biofuel Production from Acid-Impregnated Willow and Switchgrass," 2nd World Conference on Biomass for Energy, Industry and Climate, May 10-14, 2004, Rome, Italy, pp. 1467-1470.
Bigelow, M., et al., "Cellulase Production on Bagasse Pretreated with Hot Water," 2002, App Biochem and Biotech, 98-100:921-934.
Coons, R., "DSM Launches Cellulosic Biofuel Project," Oct. 27, 2008, Chemical Week, 170/33:9.
Coons, R., "Novozymes Ramps Up Focus on Second-Generation Biofuels," Oct. 27, 2008, Chemical Week, 170133:30.
Cunningham, R.L., et al., "Improved Hemicellulose Recovery From Wheat Straw," 1985, Biotech and Bioeng Symp No. 15, Seventh Symposium on Biotechnology for Fuels and Chemicals, pp. 17-26.
Dasari, R.K., et al., "The Effect of Particle Size on Hydrolysis Reaction Rates and Rheological Properties in Cellulosic Slumes," 2007, Appl Biochem and Biotech, Session 2, 137-140/1-2, 289-299, Abstract Only.
De Castro, F.B., "The Use of Steam Treatment to Upgrade Lignocellulosic Materials for Animal Feed," 1994, Thesis, University of Aberdeen, 214 pages.
Dowe, N., et al., "SSF Experimental Protocols-Lignocellulosic Biomass Hydrolysis and Fermentation, Laboratory Analytical Procedure (LAP)," Jan. 2008, NREL Technical Report, NREL/TP-510-42630, 19 pages.
Esteghlalian, A., et al., "Modeling and Optimization of the Dilute-Sulfuric-Acid Pretreatment of Corn Stover, Poplar and Switchgrass," 1997, Bioresource Technology, 59:129-136.

Fan, L.T., et al., "Evaluation of Pretreatments for Enzymatic Conversion of Agricultural Residues," 1981, Biotechnology & Bioengineering Symposium, 11:29-45 (Proceedings of the Third Symposium on Biotechnology in Energy Production and Conservation, Gatlinburg, TN, May 12-15, 1981).
Flexitray Valve Trays, Product Brochure, Koch-Glitsch, Bulletin FTCVT-01, Revised Mar. 2010, 12 pages.
Flint, S.I., et al., "Recovery of Lignin During Nonstarch Polysaccharide Analysis," 1992, Cereal Chem, 69/4:444-447.
Foody, P., "Optimization of Steam Explosion Pretreatment," 1980, Final Report to DOE, Report No. DOE/ET23050-1, Contract No. ACO2-79ET23050, Bibliographic Citation, 1 page.
Fuel Ethanol Appliation Sheet, "CELLIC Ctec and Htec2—Enzymes for Hydrolysis of Lignocellulosic Materials," Novozymes A/S, Luna No. 2010-01668-01, 9 pages.
Gea Wiegand, GmbH, Process Engineering Division, "Bioethanol Technology", Ettlingen, Germany, Company Brochure, 16 pages.
Gea Wiegand, GmbH, Process Engineering Division, "Distillation Technology", Ettlingen, Germany, Company Brochure, 16 pages.
Ghose, T.K., "Measurement of Cellulase Activities," 1987, Pure and Appl. Chem., 59/2:257-268.
Grethlein, H.E., "Chemical Breakdown of Cellulosic Materials," 1978, J. Appl. Chem. Biotechnol. 28:296-308.
Grethlein, H.E., et al., "Common Aspects of Acid Prehydrolysis and Steam Explosion for Pretreating Wood," 1991, Bioresource Technology, 36:77-82.
Grohmann, K, et al., "Optimization of Dilute Acid Pretreatment of Biomass," Proceedings of the Seventh Symposium on Biotechnology for Fuels and Chemicals, May 14-17, 1986, 24 pages.
Hames, B., et al., "Determination of Protein Content in Biomass, Laboratory Analytical Procedure (LAP)," May 2008, NREL Technical Report, NREL/TP-510-42625, 8 pages.
Hames, B., et al., "Preparation of Samples for Compositional Analysis, Laboratory Analytical Procedure (LAP)," Aug. 2008, NREL Technical Report, NREL/TP-510-42620, 12 pages.
International Search Report and the Written Opinion issued in connection with PCT Application No. PCT/CA2009/001032, mailed on Oct. 27, 2009, 11 pages.
International Search Report and the Written Opinion issued in connection with PCT Application No. PCT/CA2009/001035, dated Nov. 5, 2009, 7 pages.
International Search Report and the Written Opinion issued in connection with international application No. PCT/CA2009/001033, mailed on Oct. 30, 2009.
International Search Report and the Written Opinion issued in connection with PCT Application No. PCT/US2010/46561, dated Dec. 20, 2010, 16 pages.
International Search Report and the Written Opinion issued in PCT Application No. PCT/US20121022552, dated May 15, 2012, 18 pages.
Written Opinion of the International Searching Authority, dated Oct. 8, 2010, corresponding to International application No. PCT/CA2010/001091.
PCT International Search Report, dated Oct. 8, 2012, corresponding to International application No. PCT/CA2010/001091.
Juhasz, T., et al., "Characterization of Cellulases and Hemicellulases Produced by Trichoderma reesei on Various Carbon Sources," 2005, Process Biochem, 40:3519-3525.
Keller, F.A., et al., "Yeast Adaptation on Softwood Prehydrolysate," 1998, Appl Biochem and Biotech, 70-72:137-148.
Kolar, L., et al., "Agrochemical Value of Organic Matter of Fermenter Wastes in Biogas Production," 2008, Plant Soil Environ, 54/8:321-328.
Kumar, R., et al., "The Impact of Dilute Sulfuric Acid on the Selectivity of Xylooligomer Depolymerization to Monomers," 2008, Carbohydrate Res, 343:290-300.
Linde, M., et al., "Steam Pretreatment of Acid-Sprayed and Acid-Soaked Barley Straw for Production of Ethanol," 2006, Appl Biochem and Biotech, 129-132:546-562.
Liu, H., et al., "Lignin-Metal Complexation to Eliminate Nonproductive Enzyme Adsorption by Lignin in Unwashed Lignocellulosic Substrates," 2010, 32nd Symposium on Biotechnology for Fuels and Chemicals, 28 pages.

(56) References Cited

OTHER PUBLICATIONS

Office action issued in Canadian Application No. 2,638,152, dated Feb. 8, 2011, 4 pages.
Ohgren, K., et al., "High Temperature Enzymatic Prehydrolysis Prior to Simultaneous Saccharification and Fermentation of Steam Pretreated Corn Stover for Ethanol Production," 2007, Enzyme Microb Technol, 40/4:607-613.
Pan, X., et al., "Bioconversion of Hybrid Poplar to Ethanol and Co-Products Using an Organosolv Fractionation Process: Optimization of Process Yields," 2006, Biotech and Bioeng, 94/5:851-861.
Propax Yeast Propagation Technology, Product Brochure, Meura S.A., Edited 2009, 2 pages.
Ramsay, J.A., et al., "Biological Conversion of Hemicellulose to Propionic Acid," 1998, Enzyme Microb Technol, 22:292-295.
Schell, D.J., et al., "A Bioethanol Process Development Unit: Initial Operating Experiences and Results with a Corn Fiber Feedstock," 2004, Bioresource Technology, 91:179-188.
Sharma-Shivappa, R.R., et al, "Conversion of Cotton Wastes to Bioenergy and Value-Added Products," 2008, Transactions of the ASABE, 51/6:2239-2246.
Silwet L-77 Surfactant, Specimen Label, Helena Chemical Company, Copyright 2006, 2 pages.
Sluiter, A., et al., "Determination of Ash in Biomass, Laboratory Analytical Procedure (LAP)," NREL Technical Report, NREL/TP-510-42622, Jan. 2008, 8 pages.
Sluiter, A., et al., "Determination of Extractives in Biomass, Laboratory Analytical Procedure (LAP)," NREL Technical Report, NREL/TP-510-42619, Jan. 2008, 12 pages.
Sluiter, A., et al., "Determination of Structural Carbohydrates and Lignin in Biomass, Laboratory Analytical Procedure (LAP)," NREL Technical Report, NREL/TP-510-42618, Apr. 2008, 16 pages.
Sluiter, A., et al., "Determination of Sugars, Byproducts, and Degradation Products in Liquid Fraction Process Samples, Laboratory Analytical Procedure (LAP)," NREL Technical Report, NREL/TP-510-42623, Jan. 2008, 14 pages.
Sluiter, A., et al., "Determination of Total Solids in Biomass and Total Dissolved Solids in Liquid Process Samples, Laboratory Analytical Procedure (LAP)," NREL Technical Report, NREL/TP-510-42621, Mar. 2008, 9 pages.
Sun, L., "Silicon-Based Materials from Rice Husks and Their Applications," 2001, Ind Eng Chem Res, 40/25:5861-5877, Abstract Only, 1 page.
Superfrac High Performance Trays, Product Brochure, Koch-Glitsch, Bulletin KGSF-1, Revised Mar. 2010, 16 pages.
Taherzadeh, M. J. et al., "Pretreatment of Lignocellulosic Wastes to Improve Ethanol and Biogas Production: A Review," 2008, Int. J. Mol. Sci., (9) 1621-1651.
Teleman, et al., "Progress-Curve Analysis Shows that Glucose Inhibits the Cellotriose Hydrosysis Catalysed by Cellobiohydrolase II from Trichoderma Reesi," 1995, European J Biochem, 231:250-258.
The Artisan Dualflo Tray, Product Brochure, Artisan Industries, Inc., Bulletin 9801, Edit Date Apr. 17, 2003, 2 pages.
Thomas, S., et al., "Biofuels Program C-Milestone Completion Report," FY02, DOE Biofuels Program, Report #373, 2002, 51 pages.
Thomas, S.R., "Corn Stover Feedstock Variability," 2005, Feedstock Area Stage Gate Review Meeting, 34 pages.
Thompson, D.N., et al., "Post-Harvest Processing Methods for Reduction of Silica and Alkali Metals in Wheat Straw," 2002, 24th Symposium on Biotechnology for Fuels and Chemicals, Poster #1-30, 21 pages.
Viamajala, S.,et al., "Catalyst Transport in Corn Stover Internodes," 2005, Appl Biochem and Biotech, 129-132:509-527.
Weiss, N.D., et al., "Catalyst Impregnation for High Solids Biomass Pretreatment," 2008, AIChE Annual Meeting, 24 pages.
Yang, B., et al., "Chapter 6. Unconventional Relationships for Hemicellulose Hydrolysis and Subsequent Cellulose Digestion," 2004, Lignocellulose Biodegradation, ACS Symposium Series 889, American Chemical Society, pp. 100-125.
Zimbardi, F., et al., "Acid Impregnation and Steam Explosion of Corn Stover in Batch Processes," 2007, Ind Crops and Products, 26:195-206.
"Fuel Ethanol: Background and Public Policy Issues", (Mar. 3, 2006), CRS Report for Congress, Yacobucci, B.D., online: U.S. Department of State, Foreign Press Centre <http://fpc.state.gov/documents/organization/62837.pdf>, 26 pages.

* cited by examiner

METHOD AND APPARATUS FOR CONVEYING A CELLULOSIC FEEDSTOCK

FIELD

The invention relates to a method and apparatus for preparing a cellulosic feedstock for the subsequent production of a fermentable sugar stream from the cellulose and hemicellulose in the cellulosic feedstock wherein the fermentable sugar stream may be used for subsequent ethanol production. More specifically, the invention relates to a holding tank, and a method of utilizing the holding tank whereby bridging may be reduced or eliminated.

BACKGROUND

Several processes for the production of ethanol are known. Generally, the production of fuel ethanol involves the fermentation of sugars with yeast. Typically, the sugars are derived from grains, such as corn and wheat. The starches in the grains are subjected to enzymatic hydrolysis in order to produce the sugars, which are then subjected to anaerobic fermentation to produce ethanol.

Plant materials are a significant source of fermentable sugars, such as glucose that can be transformed into biofuels. However, the sugars in plant materials are contained in long polymeric chains of cellulose and hemicellulose. Utilizing current fermentation processes, it is necessary to break down these polymeric chains into monomeric sugars, prior to the fermenting step.

Recently, processes have been developed for utilizing cellulosic feedstock, such as corncobs, straw, and sawdust, to produce sugars for ethanol fermentation. Such processes typically comprise pre-treating the feedstock to increase the accessibility of the cellulose to hydrolysis enzymes, and subjecting the cellulose to cellulase enzyme systems to convert the cellulose into glucose.

Methods of converting plant biomass into fermentable sugars are known in the art and in general comprise two main steps: a pre-treatment step to activate the plant structure, and an enzymatic or chemical hydrolysis step to convert the polymeric chains of cellulose and hemicellulose into monomeric sugars. Several approaches have been used for the pre-treatment step, e.g., autohydrolysis, acid hydrolysis, ammonia activation, kraft pulping, organic solvent pulping, hot water pretreatment, ammonia percolation, lime pre-treatment, caustic soda pulping, or alkali peroxide pre-treatment. Early pre-treatment steps included grinding or milling the feedstock into a powder, which was then mixed with water to form a slurry.

More recently, solvent based pre-treatments, alkali pre-treatments, and acidic pre-treatments have also been described. PCT publication WO/2007/009463 to Holm Christensen describes an alternate pre-treatment, which does not involve the addition of acids, bases, or other chemicals. This pre-treatment process involves soaking the cellulosic material in water, conveying the cellulosic material through a heated and pressurized reactor, and pressing the cellulosic material to produce a fiber fraction and a liquid fraction. After pressing the cellulosic material, the cellulosic material is exposed to hydrolysis enzymes.

Each pre-treatment technology has a different mechanism of action on the plant structure, inducing either physical and/or chemical modifications. However, the main objective of the pre-treatment is to provide accessibility of the plant material to the enzymes.

SUMMARY

The commercial viability of a hydrolysis process is dependent on the character of the feedstock provided to the hydrolysis unit. Typically, this requires that a feedstock is activated such that a significant portion (e.g., greater then 75%) of the cellulose and hemicellulose of the feedstock is accessible to hydrolysis enzymes. If such an activated feedstock is provided to a hydrolysis unit, then at least 60%, preferably more than 75% and more preferably over 90% of the cellulose and hemicelluloses may be converted to monomeric sugars. This sugar rich process stream may subsequently be subjected to fermentation to produce an alcohol stream. The alcohol stream from the fermentation stage (i.e., the raw alcohol stream) may have an ethanol content of about 3-22% v/v, preferably about 5-15% and more preferably more about 8-12%.

An activated feedstock for hydrolysis is preferably prepared by auto hydrolysis, which is preferably conducted in a steam explosion reactor also known as a digester. Autohydrolysis is a process of breaking down hemicellulose and cellulose by exposure to high temperatures, steam and pressure. When performed in the presence of an acid, auto hydrolysis is known as an acid hydrolysis.

During autohydrolysis, the degree of polymerization of cellulose may be reduced from about 10,000 to about 1,500-1,000. This process is preferably carried out above the glass transition temperature of lignin (120-160° C.). Depending upon the severity of the reaction, degradation products may be produced, such as furfural, hydroxyl-methylfurfural, formic acid, levulinic acid and other organic compounds.

During a steam explosion treatment, a lignocellulosic feedstock is subjected to elevated heat (e.g., 180° C. to 220° C.) and pressure (e.g., 131 psig to 322 psig) in the presence of suitable chemicals (e.g., organic/ and/or inorganic acids, ammonia, caustic soda, sulfur dioxide, solvents etc) in a pressurized vessel. The treated lignocellulosic feedstock is then released from the pressurized vessel such that the pressure is rapidly reduced (e.g., 1 second or less). The biomass may exit the hydrolyzer into a reduced pressure, preferably atmospheric pressure and, more preferably into a vacuum. The rapid decrease in pressure results in the biomass separating into individual fibres or bundles of fibres. This step opens the fibre structure and increases the surface area. The lignin remains in the fibre along with cellulose and residual hemicellulose. Accordingly, the explosive release of pressure, combined with the high temperature and pressure treatment results in the physicochemical modification of the lignocellulosic feedstock that is then suitable for feeding to a hydrolysis unit.

In order for the steam explosion process to be able to produce an activated feedstock that is capable of producing such a sugar rich process stream, the temperature and moisture level of the cellulosic feedstock that is fed to a steam explosion reactor preferably is relatively uniform and preferably has a temperature from about 50 to about 70° C., and more preferably 50-65° C. and a moisture content from about 30 to about 60 wt % (preferably 45 to about 55 wt %). Moisture content is the quantity of water contained in a material, and on a weight basis, is the weight of water in the material divided by the mass of the material.

Without being limited by theory, it is believed that an unexpected increase in the conversion of the feedstock to fermentable sugars may be achieved if the moisture content of the feedstock fed to the steam explosion reactor is lower, provided that sufficient water is present for hydrolyzing and/or activating the feedstock. If the feedstock is too dry, then there may be insufficient water molecules present in the fiber and hence not all of the feedstock will be activated and/or hydrolyzed (i.e., the hydrolysis reaction/activation will not occur at all possible sites). Accordingly, it might be presumed that a substantial excess of water should be used to ensure water molecules are available at each hydrolysis/activation site. Surprisingly, it has been determined that if the cellulosic feedstock that is fed to a steam explosion reactor has an excess of moisture then a smaller percentage of the available sites of the feedstock are activated/hydrolyzed than would be expected. It is believed that this is due to the high moisture content acting as a barrier to heat transfer through the fiber structure. The external fiber reaches the process temperature far in advance to the internal fiber, hence resulting in very uneven heat transfer and the resulting uneven autohydrolysis reaction. Further, during the autohydrolysis process additional water may be provided to the process by way of direct injected steam in order to raise the fiber temperature from the inlet temperature to the outlet temperature of the reactor. If the inlet moisture content of the fiber is at saturation, then the additional water will be free water in the autohydrolysis reactor resulting in washing of the soluble hemicellulose from the fiber and causing subsequent accumulation of hemicellulose within the reactor, Over time, the accumulated hemicellulose will tend to break down to inhibitor compounds and deposit degraded sugars on the internal components of the reactor. These deposits will become an obstruction to the flow of the biomass.

It has also been determined that if the cellulosic feedstock that is fed to a hydrolyzer has a temperature that is too high, then some percentage of the hemicellulose sugars will be degraded to inhibitory compounds prior to starting the autohydrolysis reaction and further amounts during the autohydrolysis reaction itself. Conversely, if the fiber is too cold entering the hydrolyzer, the first one third to one half of the reactor vessel may act as a preheating device rather than as a hydrolyzer, resulting in incomplete autohydrolysis. Accordingly, it is preferred to have very consistent fiber temperature year round as well as from night to day time operation, for the fiber that is fed to the hydrolyzer.

Alternately, and in addition, it is preferred that the fiber in the feedstock fed to the autohydrolysis unit have a relatively uniform temperature profile. For example, it is preferred that the core of the blocks of material have a temperature that is within 80%, more preferably 90%, most preferably 95% of the temperature of the exterior surface of the material. Accordingly, for example, if the temperature of the exterior surface of the material is from 50 to 70° C., then the temperature of the core of the material is preferably from 45 to 63° C.

It has also been determined that the fiber requires time for the moisture that is added to become equilibrated throughout the entire fiber particle. It has been determined that under laboratory conditions, it may take from 5 to 9 minutes to equilibrate the moisture content of the fiber. Under industrial conditions it will be longer. Preferably, the autohydrolysis reaction time in the vessel is typically about 5 to 6 minutes or less. It is preferred that the fiber in the feedstock fed to the autohydrolysis unit have a relatively uniform moisture profile. For example, it is preferred that the core of the blocks of material have a moisture content that is within 80%, more preferably 90%, most preferably 95% of the moisture content of the exterior surface of the material. Accordingly, for example, if the moisture content of the exterior surface of the material is from 45 to 55 wt %, then the moisture corttent of the core of the material is preferably from 40.5 to 49.5 wt %.

A feedstock having a moisture content from about 45 to about 55 wt % may be prepared by obtaining relatively dry plant material which is broken down into small chips, e.g., from about 0.05 to about 2 inches, and then combining the chip with water (e.g., steam and/or a fine mist spray, such as droplets of water of between 600μ and 900μ in diameter). This material may then be transported to a hydrolysis or auto hydrolysis reactor. This material is difficult to transport as the material is essentially a solid (having insufficient water to form even a slurry). Accordingly, the material has a tendency to interlock and may result in process vessels or flow passages between equipment becoming blocked.

Embodiments of the present invention provide a method and apparatus for transporting a cellulosic feedstock. The method and apparatus relate to a holding tank that can be positioned downstream from a cellulosic feedstock pre-treatment process, and that can be utilized to further prepare the cellulosic feedstock for, e.g., auto hydrolysis or hydrolysis.

In one broad aspect, a method of preparing a cellulosic feedstock for ethanol production is provided. The method comprises passing the cellulosic feedstock through an impregnation chamber to an outlet of the impregnation chamber, passing the cellulosic feedstock from the outlet of the impregnation chamber to a holding tank having an inlet and an outlet, and conveying the cellulosic feedstock downwardly and laterally as it travels through the holding tank.

Embodiments in accordance with this broad aspect may be advantageous because the lateral movement of the feedstock assists in preventing the feedstock from plugging the apparatus. In particular, if the holding tank had walls that extended vertically and defined a vertical passage therethrough, then the feedstock would travel vertically downwardly. Due to the nature of the feedstock, the feedstock has a tendency to bridge the vertically extending passage, resulting in some, or possibly all, of the passage becoming blocked. Bridging of the passage can result in the need for manual intervention, as well as monitoring, to ensure that feed material is supplied to downstream process equipment on a continuous basis. Further, if the holding tank is provided with a steam jacket, overly long holdup of material in the holding tank could result in degradation of some of the cellulose and hemicellulose in the feedstock.

In some embodiments, the method further comprising maintaining a temperature in the holding tank between about 50° Celsius and about 75° Celsius. Such embodiments may be advantageous because the elevated temperature may prepare the feedstock exiting the holding tank to be at a predetermined temperature for the next process stage. Further, if the feedstock entering the holding tank is at the predetermined temperature for the next process stage, the feedstock may be maintained at a desired temperature as it passes through the holding tank.

In some embodiments, the cellulosic feedstock moves from the inlet to the outlet of the holding tank in about 10 to about 30 minutes.

In some embodiments, the inlet of the holding tank is disposed at an elevation above the outlet of the holding tank, and the cellulosic feedstock migrates from the inlet towards the outlet of the holding tank under the force of gravity.

In some embodiments, the holding tank comprises an outlet, and the method further comprises conveying the cellulosic feedstock laterally across the outlet.

In some embodiments, the step of conveying the cellulosic feedstock laterally across the outlet comprises actively withdrawing the cellulosic feedstock from essentially an entirety of the outlet.

In some embodiments, the step of conveying the cellulosic feedstock laterally across the outlet comprises withdrawing a generally equal amount of cellulosic feedstock from each portion of the outlet.

In some embodiments, the step of conveying the cellulosic feedstock laterally across the outlet comprises withdrawing a first portion of the cellulosic feedstock in a first lateral direction and withdrawing a second portion of the cellulosic feedstock in a second lateral direction.

In another broad aspect, a holding tank for a cellulosic feedstock is provided. The holding tank apparatus comprises at least one sidewall defining a passage. The passage has an upper portion and a lower portion, and the lower portion has a greater cross-sectional area than the upper portion. At least one inlet is provided adjacent the upper portion, and at least one outlet is provided adjacent the lower portion, at an elevation below the inlet.

Embodiments in accordance with this broad aspect may be advantageous because providing the lower portion with a greater cross-sectional area than the upper portion may prevent cellulosic material from adhering or sticking to the sidewalls as the cellulosic material passes through the holding tank. Accordingly, each portion of cellulosic feedstock that passes through the holding tank may have essentially the same residence time in the passage. This may be advantageous in helping to ensure that the feedstock exiting the holding tank has a more uniform temperature and/or moisture content.

In some embodiments, the sidewalls comprise a first sidewall and a second sidewall opposed to the first sidewall, and the first and second sidewalls diverge relative to each other from the upper portion to the lower portion.

In some embodiments, the sidewalls comprise a third sidewall and a fourth sidewall opposed to the third sidewall. The third and fourth sidewalls extend between the first and second sidewalls, and the third and fourth sidewalls diverge relative to each other from the upper portion to the lower portion.

In some embodiments, the holding tank apparatus further comprises at least one discharge member adjacent the outlet. The discharge member may serve to withdraw the cellulosic feedstock from the outlet and direct it towards one or more hydrolysis reactors.

In some embodiments, the at least one discharge member comprises a base and an open top that is at least as large as, and is in vertical registration with, the outlet, and at least a first discharge member outlet that is laterally positioned.

In some embodiments, the at least one discharge member comprises at least one screw conveyor mounted above the base.

In some embodiments, the at least one discharge member comprises a first pair of screw conveyors, and each screw conveyor in the first pair rotates about respective first and second generally parallel axes. In some embodiments, the axes extend at an angle of less than 45° relative to horizontal. In further embodiments, the axes are generally horizontal.

In some embodiments, the screw conveyors are rotated in the same direction and feed material from above towards the first discharge member outlet.

In some embodiments, the screw conveyors have a first pitch adjacent the first discharge member outlet, and a second pitch narrower than the first pitch distal to the first discharge member outlet. Such embodiments may be advantageous because a generally equal amount of feedstock may be withdrawn from each portion of the lower end.

In some embodiments, the screw conveyors each have a first flight and a second flight, and the first flight has a first pitch and is disposed adjacent the first discharge member outlet, and the second flight has second pitch narrower than the first pitch and is disposed along the shaft upstream from the first flight. In some further embodiments, each screw conveyor comprises a third flight intermediate the first and second flights, and the third flight has an intermediate pitch that is wider than the first pitch and narrower than the wider pitch.

In some embodiments, the discharge member further comprises a second pair of screw conveyors. In some such embodiments, the screw conveyors of the second pair are rotatable about parallel axes. Preferably, the axes are generally horizontal. Further, each screw conveyor in the second pair preferably rotates in the same direction.

In some embodiments, the second pair of screw conveyors urges material from above towards a second discharge member outlet that is laterally positioned and spaced away from the first discharge member outlet.

In some embodiments, the second discharge member outlet is laterally opposed to the first discharge member outlet. In some further embodiments, the screw conveyors of first pair rotate opposite to the screw conveyors of second pair.

In some embodiments, the holding tank apparatus further comprises a heating jacket provided on at least a portion of the sidewalls. In some embodiments, the heating jacket is provided on the sidewalls.

BRIEF DESCRIPTION OF THE DRAWINGS

These and other advantages of the present invention will be more fully and particularly understood in connection with the following description of the preferred embodiments of the invention in which.

DETAILED DESCRIPTION

The cellulosic feedstock is preferably a lignocellulosic feedstock. A lignocellulosic feedstock is derived from plant materials. As used herein, a "lignocellulosic feedstock" refers to plant fiber containing cellulose, hemicellulose and lignin. In some embodiments, the feedstock may be derived from trees, preferably deciduous trees such as poplar (e.g., wood chips). Alternately or in addition, the feedstock may also be derived from agricultural residues such as, but not limited to, corn stover, wheat straw, barley straw, rice straw, switchgrass, sorghum, sugarcane, bagasse, rice hulls and/or corn cobs. Preferably, the lignocellulosic feedstock comprises agricultural residues and wood biomass, more preferably wood biomass and most preferably hardwoods. The applicants contemplate other sources of plant materials comprising cellulose, hemicellulose and lignin for use in deriving lignocellulosic feedstocks and any of those may be used.

The lignocellulosic feedstock is preferably cleaned, e.g., to remove ash, silica, metal strapping (e.g., from agricultural products), stones and dirt. The size of the components of the lignocellulosic feedstock may also be reduced. The size of the components of the feedstock may be from about 0.05 to about 2 inches, preferably from about 0.1 to about 1 inch, and more preferably from about 0.125 to about 0.5 inches in length. For example, the cellulosic feedstock may comprise fibers, e.g., chopped straw, of a length of between about 4 mm and about 7 mm. Any process machinery that is able to crush, grind or otherwise decrease the particle size may be utilized.

The feedstock is preferably treated with water as to have a moisture content upon entry to holding tank 100 of from about 30 to about 60 wt %, Same as the other ones preferably from about 45 to about 55 wt %. For example, referring to FIGS. 1 and 2, an embodiment of a holding tank 100 of the present invention is shown wherein the holding tank 100 is positioned downstream from an impregnation chamber 10, which is preferably used to pre-treat the feedstock prior to the feedstock entering holding tank 100. Impregnation chamber 10 is preferably configured to pre-treat the cellulosic feedstock, for example by moistening and/or heating the cellulosic feedstock.

Figure 2:
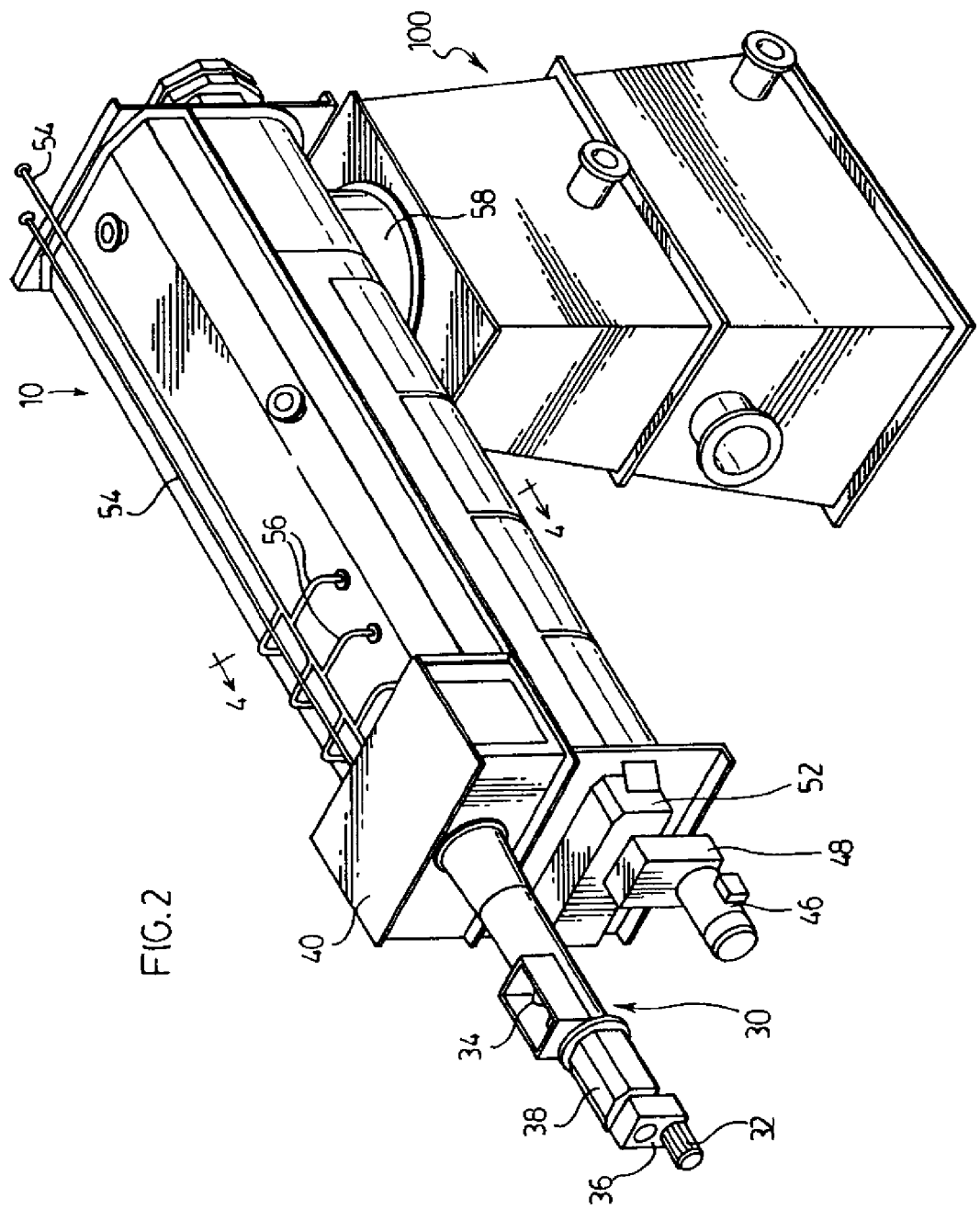
FIG. 2 is a perspective illustration of the impregnation chamber shown in FIG. 1.
Figure 3:
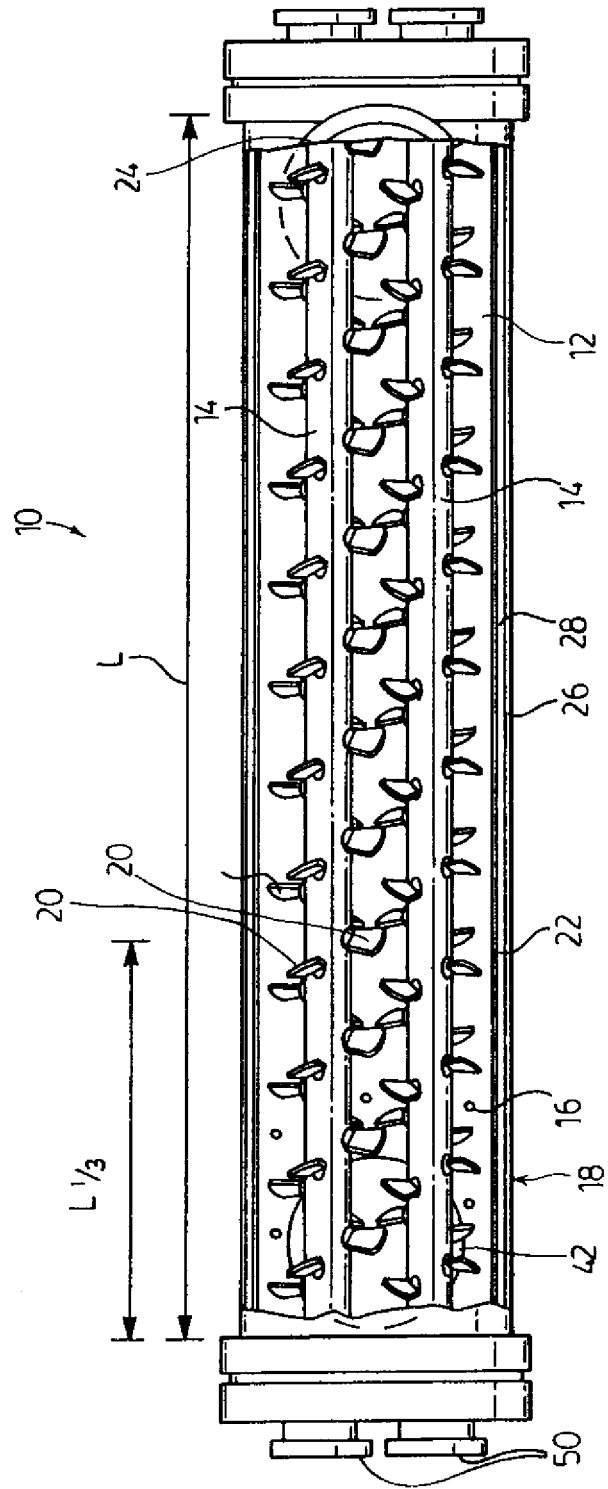
FIG. 3 is a top cutaway view of the impregnation chamber of FIG. 1.
Figure 4:
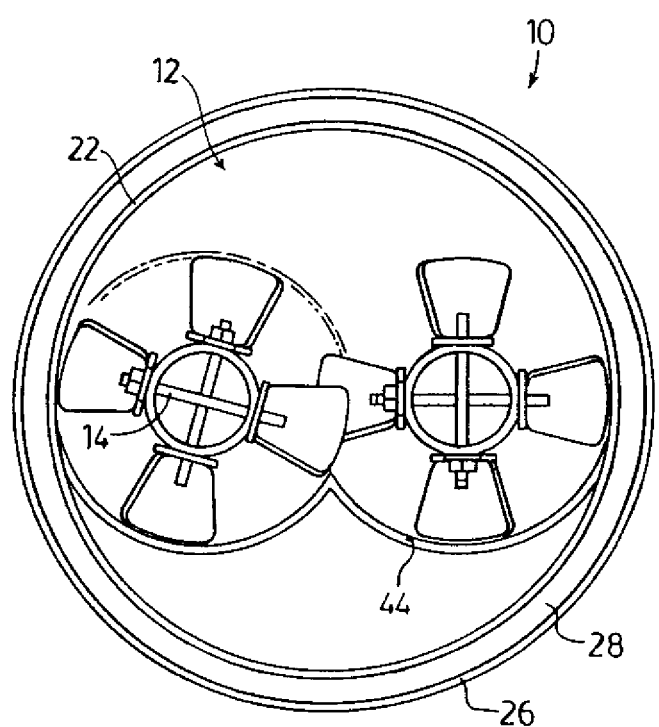
FIG. 4 is a cross section taken along line 44 in FIG. 2.

A preferred impregnation chamber 10 is exemplified in FIGS. 2-4, impregnation. As shown therein, impregnation chamber 10 may comprise an inlet 11, one or more conveyance members 12 for urging the cellulosic feedstock along the length of the chamber, one or more moisture injection ports 14, which may be provided on paddles 20 of conveyance member 12 and/or inner wall 22 of impregnation chamber 10, for injecting moisture into the cellulosic feedstock, one or more heating jackets 16 provided outward of inner wall 22 for heating the cellulosic feedstock, and an outlet 18. In order to prevent material stagnating in impregnation chamber 10, impregnation chamber 10 may have a bottom wall 24 that has two or more portions each of which has a conveyance member 12 associated therewith. Bottom wall 24 and conveyance member 12 are preferably configured such that bottom wall 24 is swept as conveyance member 12 rotates. For example, as exemplified in FIG. 4, bottom wall 24 may be scallop shaped, e.g., have two inverted arches or troughs. Further details regarding various embodiments of optional impregnation chamber 10 may be found in co-pending U.S. patent application Ser. No. 12/181,569, filed on Jul. 29, 2008, the disclosure of which is incorporated herein by reference in its entirety.

After the cellulosic feedstock is optionally pre-treated in impregnation chamber 10, it is directed to holding tank 100, where it is held or contained for a residence time, such that, for example, moisture added in impregnation chamber 10 has sufficient time to penetrate into the feedstock so that the feedstock is ready for downstream processing. Alternately, or in addition, the feedstock may require additional time for all portions of the feedstock to be raised to a predetermined temperature that is suitable for downstream processing. Alternately, the feedstock entering holding tank 100 may be at the predetermined conditions for downstream processing and holding tank is used as a reservoir to hold prepared feedstock such that downstream processes may operate on a continuous basis. From holding tank 100, the cellulosic feedstock may be directed to one or more downstream process units, preferably auto hydrolysis and/or hydrolysis reactors (not shown), such that the cellulose may be hydrolyzed to produce sugars that are suitable for fermentation to ethanol.

Figure 1:
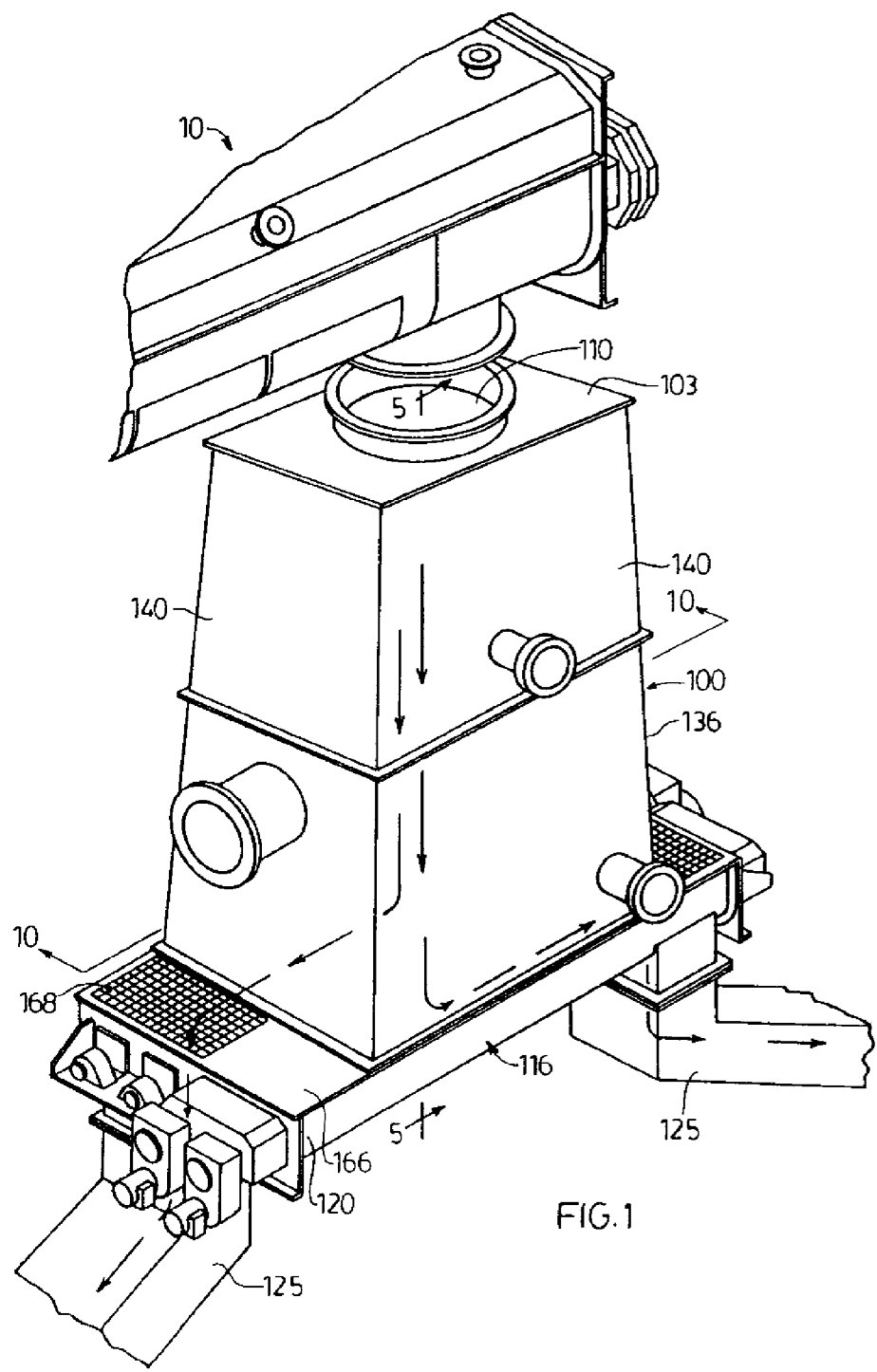
FIG. 1 is a perspective illustration of an embodiment of a holding tank of the present invention, showing an impregnation chamber that may be positioned upstream from the holding tank.
Figure 5:
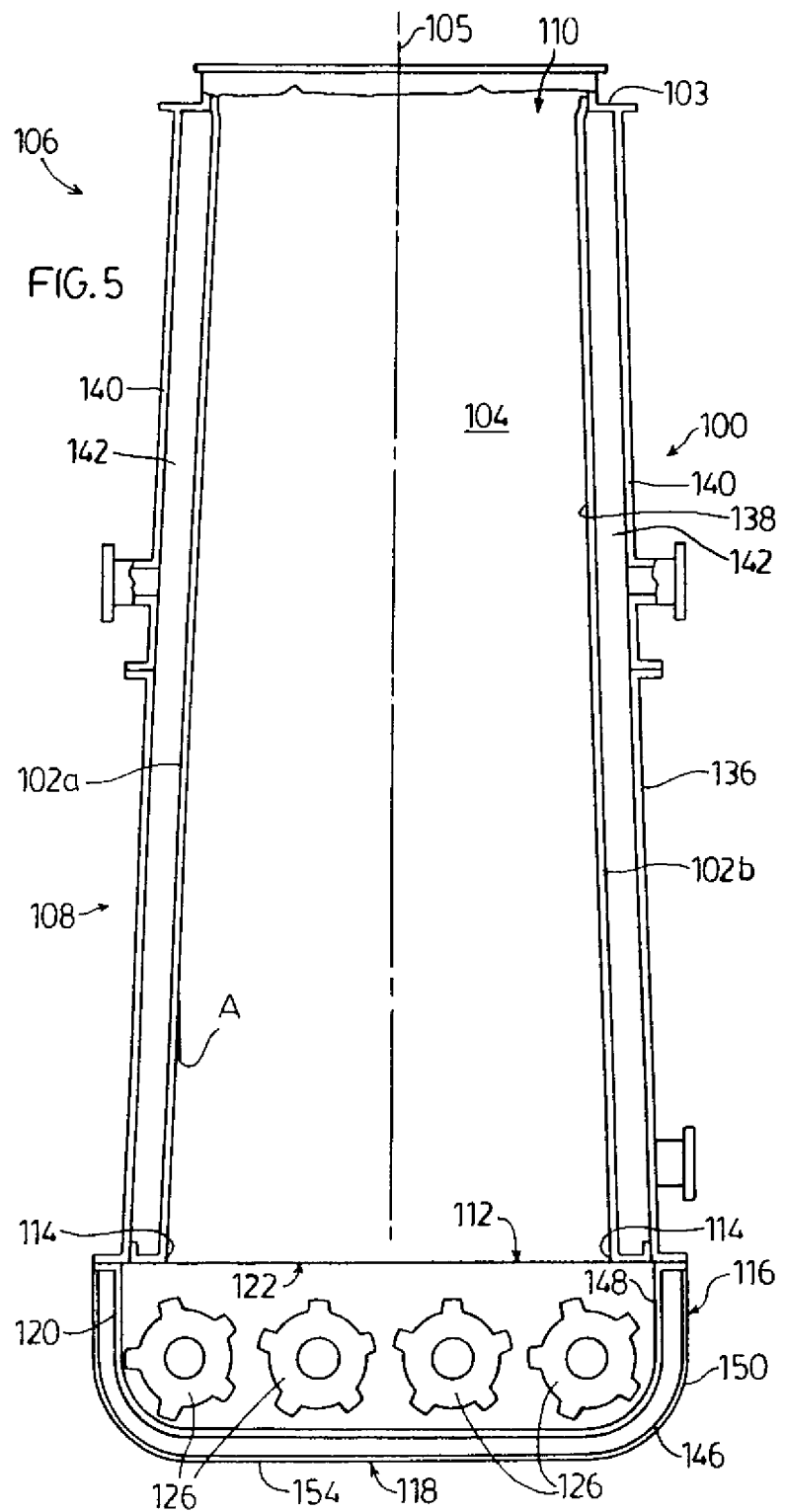
FIG. 5 is a cross section taken along line 5-5 in FIG. 1.

As exemplified in FIGS. 1 and 5, holding tank 100 is oriented such that the passage through holding tank 100 extends generally downwardly and the passage therethrough is configured so as to reduce, and preferably essentially prevent, bridging of feedstock in holding tank 100. Accordingly, it is preferred that the passage through holding tank 100 extends generally downwardly and that the passage has a greater cross sectional area at the lower end then the upper end. More preferably, the cross sectional area continually increases in the downward direction. This may be achieved by constructing the passage of the holding tank with one or more walls that diverge in the downward direction.

If the feedstock passing downwardly through holding tank interlock, it may form a blockage by a process known as bridging. The blockage may extend all the way across the passage in holding tank 100 thereby preventing downward movement of feedstock and causing a gap in the supply of feedstock to the downstream process unit. Alternately, it may block only part of the passage. In any event, intervention would then be required to remove the blockage. The interruption of feedstock delivery to the downstream process unit could require part of a plant to be shut down while the blockage is removed thereby reducing throughput and also requiring the plant to be brought back to steady state operating conditions once the blockage is cleared. Accordingly, the holding tank may require monitoring to permit intervention at an early stage should bridging occur. By increasing the cross sectional area in the downstream direction, the tendency of the feedstock to form a blockage of the passage is reduced and may be eliminated.

Figure 10:
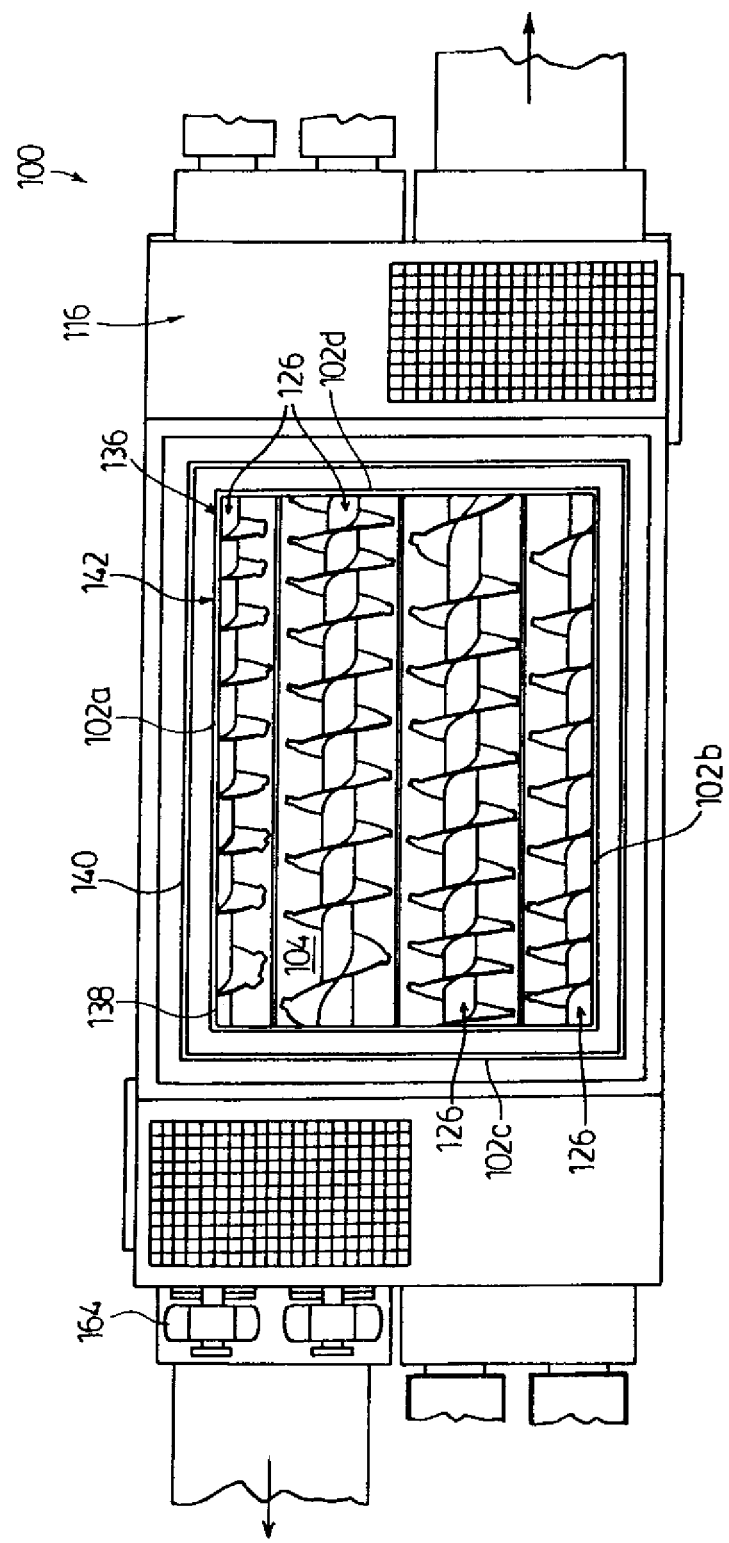

As exemplified in FIGS. 5 and 10, holding tank 100 comprises at least one sidewall 102, which defines a volume or passage 104. In the embodiment shown, holding tank 100 comprises four sidewalls, namely front wall 102a and a spaced apart opposed rear wall 102b, and a side wall 102c and a spaced apart opposed side wall 102d, and further comprises a top wall 103. Accordingly, passage 104, which is defined by sidewalls 102a, 102b, 102c and 102d is rectangular in transverse section. In other embodiments, holding tank 100 may comprise, for example, a single rounded sidewall so as to have a transverse section that is circular, elliptical or the like. It will be appreciated that any other transverse section may be utilized.

Passage 104 is preferably longitudinally extending, for example along axis 105, and comprises an upper portion 106, and a lower portion 108. Passage 104 preferably extends vertically. However passage may extend generally vertically (i.e., at an angle to the vertical such that feedstock will flow downwardly therethrough under the force of gravity). In some embodiments, passage 104 may have a length along axis 105 of between about 5 ft and about 10 ft.

An inlet 110 is provided adjacent upper portion 106, and an outlet 112 is provided adjacent lower portion 108, at an elevation below the inlet 110. In the embodiment shown, inlet 110 is defined by an opening in top wall 104, and outlet 112 is defined by the lower ends 114 of sidewalls 102. It will be appreciated that inlet 110 may comprise the entirety of the top end of holding tank 100 and accordingly, a top surface 103 may not be required. It will be appreciated that in the preferred embodiment, no lower surface is provided for passage 104 and that the lower end of passage 104 is open. Accordingly, feedstock may flow downwardly through passage 104 unimpeded until it encounters feedstock stored in holding tank 100 or until it encounters discharge member 116. As exemplified, inlet 110 is in fluid communication with and receives cellulosic feedstock from outlet 18 of impregnation chamber 10, and outlet 112 is in fluid communication with and directs cellulosic feedstock to one or more auto hydrolysis reactors (not shown).

Referring still to FIG. 5, the lower end of passage 104 has a greater cross sectional area than upper end of passage 104. That is, a transverse cross section taken through passage 104 adjacent outlet 112 has a greater cross sectional area than a transverse section taken through passage 104 adjacent inlet 110. For example, the cross sectional area taken adjacent outlet 112 may have an area of between about 40 ft$^2$ and about 60 ft$^2$ and the cross sectional area taken adjacent inlet 110 may have an area of between about 20 ft$^2$ and about 40 ft$^2$.

Sidewalls 102 may be configured in a variety of ways in order to provide lower portion 108 with a greater cross sectional area than upper portion 106. In the embodiment shown, sidewall 102a and sidewall 102c are opposed to each other, and diverge from each other going from inlet 110 to outlet 112. Further sidewall 102b and sidewall 102d are opposed to each other, and diverge from each other going from inlet 110 to outlet 112. Accordingly, passage 104 is substantially frusto-pyramidal, and lower portion 108 has a greater cross sectional area than upper portion 104. In an alternate embodiment, sidewalls 102a and 102c may extend substantially parallel to each other, and sidewalls 102b and 102d may diverge from each other. In yet another alternate embodiment, holding tank 100 may comprise a single rounded sidewall defining a frustoconical passage 104. In yet another embodiment, sidewalls 102 may be stepped. It is preferred that sidewalls 102 continually diverge and that they continually diverge for the entire length of passage 104 as exemplified. Preferably, they diverge at an angle A from the vertical from about 1° to about 20°, preferably from about 2° to about 5°. It will also be appreciated that inner surface 138 of sidewalls 102 are preferably smooth and clear of projections that could be a source causing bridging to occur.

Providing lower portion 108 with a greater cross sectional area than upper portion 106 may aid in preventing cellulosic material from adhering or sticking to sidewalls 102 as the cellulosic material passes through holding tank 100. Accordingly, each portion of cellulosic feedstock that passes through holding tank 100 may have essentially the same residence time in passage 104.

In some embodiments, the feedstock may travel directly downwardly to the next process unit. In such a case, it is preferred the flow passage continually increase in cross sectional area (as opposed to using a hopper). However, it is preferred that the feedstock, after traveling downwardly through passage 104, is conveyed laterally (transverse to axis 105). Further, it is preferred that the feedstock is actively withdrawn from holding tank 104 instead of permitting the feedstock to passively flow out therefrom. Accordingly, in the exemplified embodiment, holding tank 100 is seated on a discharge member 116 adjacent outlet 112. Discharge member 116 is configured to convey the celluslosic material laterally across outlet 112 to actively withdraw the cellulosic feedstock from holding tank 100.

Referring to FIGS. 5 to 8, in the embodiment shown, discharge member 116 comprises a base 118, sidewalls 120, and an open top 122. Open top 122 is preferably at least as large as outlet 112, and is in vertical registration with outlet 112, such that material passing through outlet 112 may pass directly downwardly through open top 122. It will be appreciated that in alternate embodiments, sidewalls 102 of passage 104 may provide the sidewalls of discharge member 116. That is, sidewalls 102 may extend beyond outlet 112. Accordingly, in such an embodiment, outlet 112 of passage 104 may not be defined by ends 114 of sidewalls 102, and rather, may be defined by a portion of sidewalls 102 above ends 114.

Discharge member 116 may use any transport mechanism known in the art to actively transport feedstock laterally from outlet 112. For example, a discharge member 116 may comprise an auger, a screw conveyor, drag line conveyor, paddle conveyor or the like that extends transversely to axis 105. Discharge member 116 comprises at least a first discharge member outlet 124, through which cellulosic feedstock exits discharge member 116. Cellulosic feedstock exiting discharge member outlet(s) 124 may pass into one or more conduits 125, which may, for example, lead to one or more, e.g., auto hydrolysis reactors (not shown). Preferably more then one outlet 124 is provided. An advantage of having more then one outlet is that two treated feedstock stream may be provided from holding tank 100.

Figure 6:
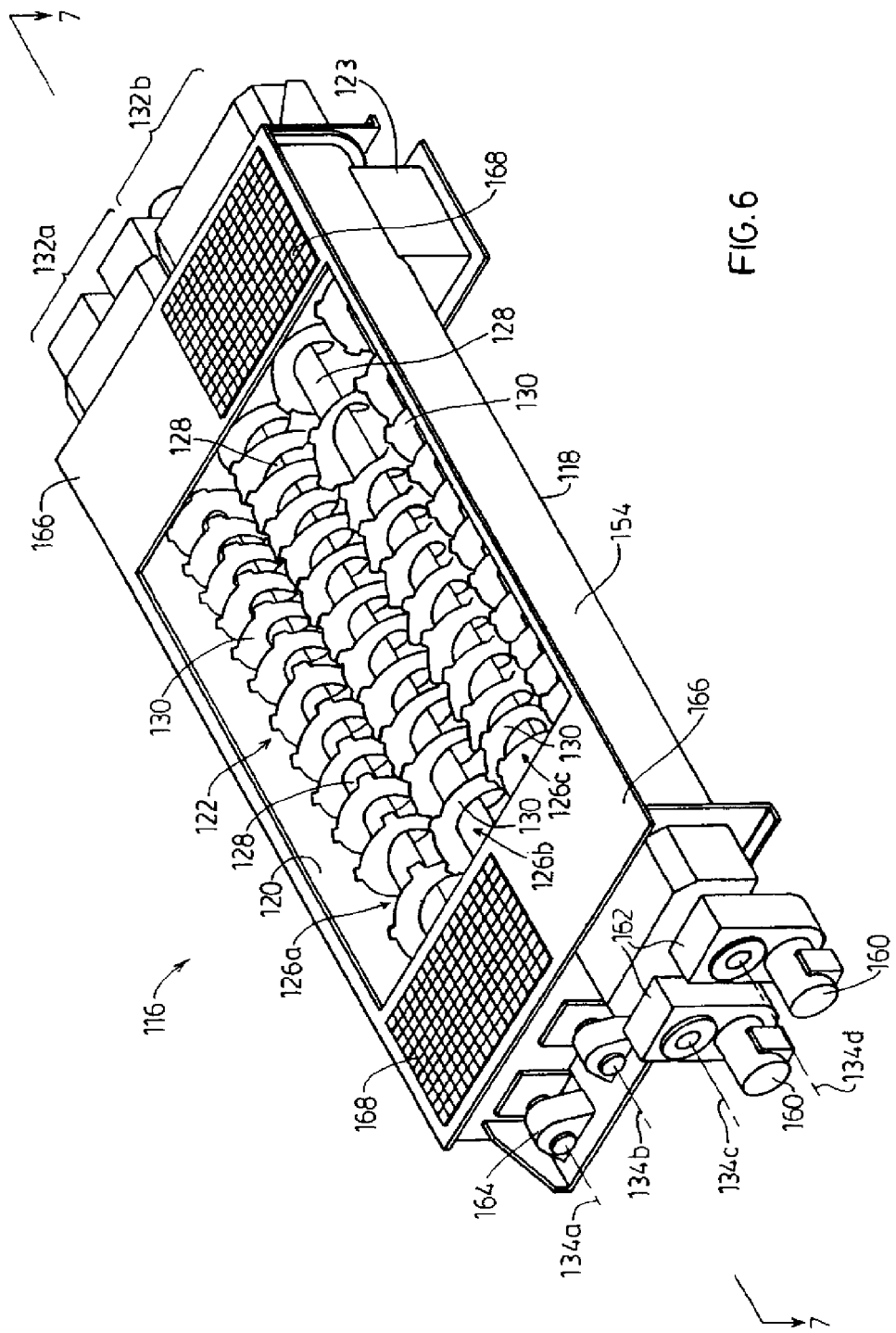
FIG. 6 is a perspective view of an embodiment of discharge member of the present invention, shown removed from a holding tank.
Figure 7:
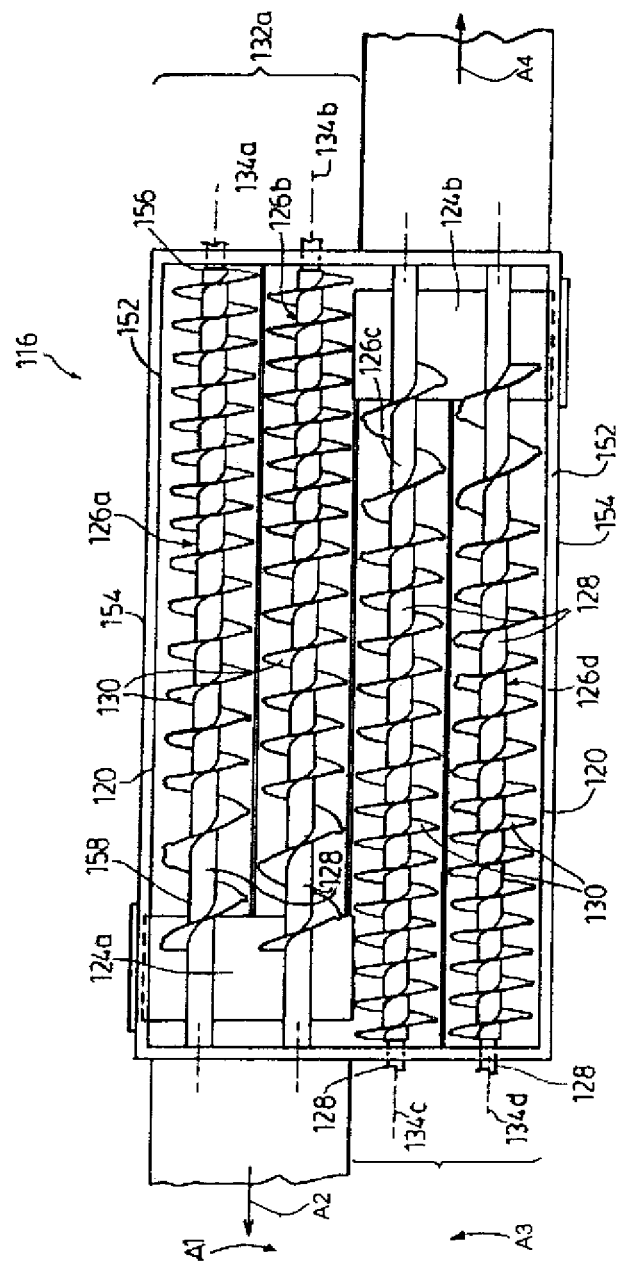
FIG. 7 is a cross-section taken along line 7-7 in FIG. 6.
Figure 8:
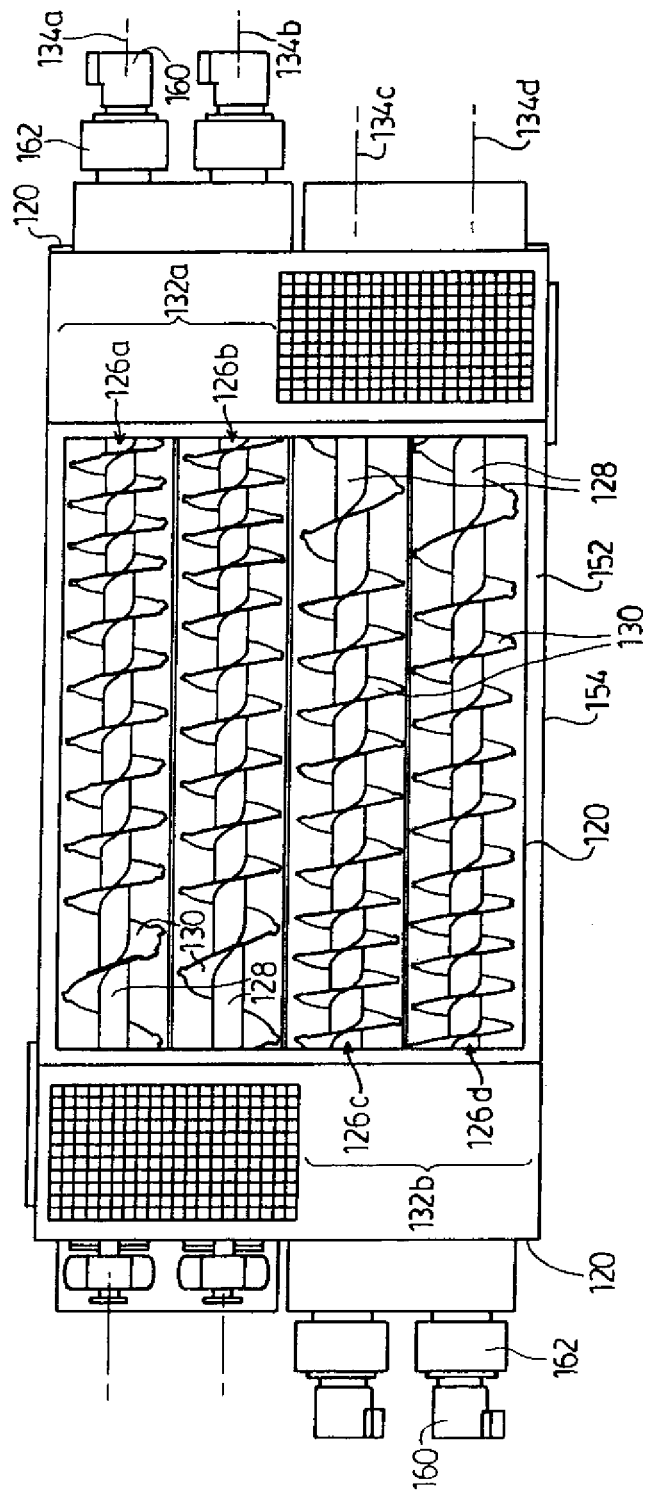
FIG. 8 is a top view of the discharge member of FIG. 6.

As exemplified, discharge member 116 comprises two discharge member outlets 124a, 124b (see FIG. 7). Preferably, each outlet 124 is positioned such that it is not underneath passage 104 (laterally spaced from passage 104) and preferably more then one outlet 124 is provided. An advantage of positioning outlets 124 laterally from passage 104 is that feedstock may be withdrawn from all of outlet 112 and, more preferably, evenly from across outlet 112. Further, discharge member outlets 124a and 124b are preferably positioned on opposite sides of discharge member 116. Accordingly, discharge member outlets 124a and 124b may direct cellulosic material to two different, e.g., auto hydrolysis reactors, positioned on opposite sides of holding tank 100. As exemplified in FIGS. 1, 6 and 7, discharge member 116 may have upper wall 166 that extends over the top surface of discharge member 116 positioned laterally of holding tank 100. Top wall 166 may cover the portion of screw conveyor 126 positioned laterally of holding tank 100. Optionally, a grate 168, or other member that provides a window, may be positioned in top wall 166 above outlet 124. Grate 168 permits a worker to observe the travel of feedstock into conduits 125.

Discharge member 116 preferably comprises at least one screw conveyor 126 mounted above base 118. As exemplified, each screw conveyor 126 comprises a shaft 128 and at least one helical flighting 130 extending about the shaft, and is configured to rotate to engage material exiting outlet 112, and to convey it towards one of the discharge member outlets 124. Shaft 128 may be rotatably mounted by any means known in the art. As exemplified, shaft 128 has one end journalled in a bearing housing 164 and a second end journalled in a transmission housing 162. In the embodiment shown, discharge member 116 comprises a plurality of screw conveyors 126, which are arranged in pairs. First pair 132a comprises screw conveyors 126a and 126b, which rotate about respective first 134a and second 134b generally parallel axes, and second pair 132b comprises screw conveyors 126c, and 126d, which rotate about respective first 134c and second 134d generally parallel axes. Each of axes 134 are preferably horizontal, but may be at an angle of up to 45° or greater from the horizontal. Accordingly, screw conveyors 126a and 126b transport treated feedstock to outlet 124a and screw conveyors 126c and 126d transport treated feedstock to outlet 124b, which is on an opposed side to outlet 124a. It will be appreciated that screw conveyors 126a, 126b, 126c and 126d extend under essentially all of outlet 112. Therefore, the screw conveyors 126 preferably withdraw treated feedstock for all portions of outlet 112. Alternately, or in addition, each outlet 124 may have one or more screw conveyors 126 or other transport member associated therewith.

Referring still to FIG. 7, as exemplified, screw conveyors 126a and 126b of first pair 132a may each be rotated in a direction indicated by arrow A1, to feed material from above towards discharge member outlet 124a. Further, screw conveyors 126c and 126d of second pair 132b may each be rotated in a direction indicated by arrow A2, to feed material from above towards discharge member outlet 124b.

In order to permit each screw conveyors 126 to be rotated, in a particular direction of rotation, each screw conveyor may be driven by its own drive motor 160. As shown in FIGS. 6 and 7, each shaft 128 extends outwardly past sidewall 120 into a transmission housing 162 wherein motor 160 is drivingly connected to shaft 128. Any driving linkage known in the art may be used. It will be appreciated that in an alternate embodiment, a single motor 160 may drive two or more shafts.

Accordingly, as exemplified, discharge member outlets 124a and 124b are positioned on laterally opposite sides of discharge member 116, and each helical fighting 130 is right-handed. Accordingly, direction A1 and direction A2 are opposite to each other. However, in alternate embodiments, discharge member outlets 124a and 124b may be positioned on the same lateral side as each other. In such an embodiment, directions A1 and A2 may be substantially the same. In yet further alternate embodiments, the helical flighting 130 of the first pair 132a of screw conveyors 126a, 126b, may be right handed, and the helical flighting 130 of the second pair 132b of screw conveyors 126c, 126d may be left handed. Accordingly, in such an embodiment, the first pair may rotate in the same direction as the second pair, and convey material in an opposite direction. It will be appreciated that each pair of screw conveyors 126 may be configured such that they rotate in opposite directions. For example, screw conveyor 126a may be configured to rotate clockwise and screw conveyor 126b may be configured to rotate counterclockwise.

Preferably, the helical flighting 130 of each screw conveyor has a first pitch adjacent its respective discharge member outlet 124 (i.e. the discharge member outlet towards which it conveys cellulosic feedstock), and a second pitch distal to its respective discharge member outlet 134 narrower than the first pitch. That is, screw conveyors 126a and 126b have a first pitch at end 158 adjacent discharge member outlet 124a, and a second narrower pitch at the end 156 that is distal to discharge member outlet 124a; and screw conveyors 126c and 126d have a first pitch adjacent discharge member outlet 124b, and a second narrower pitch distal to discharge member outlet 124b.

In the embodiments shown, the pitch of each helical flighting 130 gradually becomes wider towards each discharge member outlet 124. For example, the pitch may vary gradually from between about 4 inches and about 8 inches at the distal end 156 of screw conveyor 126 to between about 14 inches and about 16 inches the end 158 of screw conveyor 126 adjacent discharge member outlet 124. In alternate embodiments, an abrupt transition between wider and narrower regions of flighting may occur. For example, each screw conveyor may comprise a first flight adjacent a discharge member outlet 124 and a second flight upstream from the first flight. The first flight may have a first constant pitch, for example of between about 14 inches and about 18 inches, and the second fight may have a second constant pitch narrower than the first constant pitch, for example of between about 4 inches and about 8 inches. In a further embodiment, a third intermediate flight having a third constant pitch wider than the second flight and narrower than the first flight may be positioned between the first flight and the second flight. The third flight may have a pitch of between about 6 inches and about 10 inches, for example.

Providing each screw conveyor with a narrower pitch distal to the discharge member outlet may allow for substantially equally amounts of material to be withdrawn from each portion of outlet 112. That is, material deposited in screw conveyor 126 at the distal end 156 will be conveyed towards the respective outlet 124 for that screw conveyor. As that material is transported laterally, the pitch of the screw increases permitting additional material to be deposited directly in the screw conveyor from outlet 112. Further increases in the pitch will permit additional portions of the material to fall into screw conveyor. The portion or portions of the screw conveyor closer to outlet 124 (in the direction of transport) have a wider pitch such that it may accommodate material conveyed from the distal region, as well as material deposited directly thereon from passage 104. Accordingly, feedstock is withdrawn from across all of outlet 112.

Figure 9:
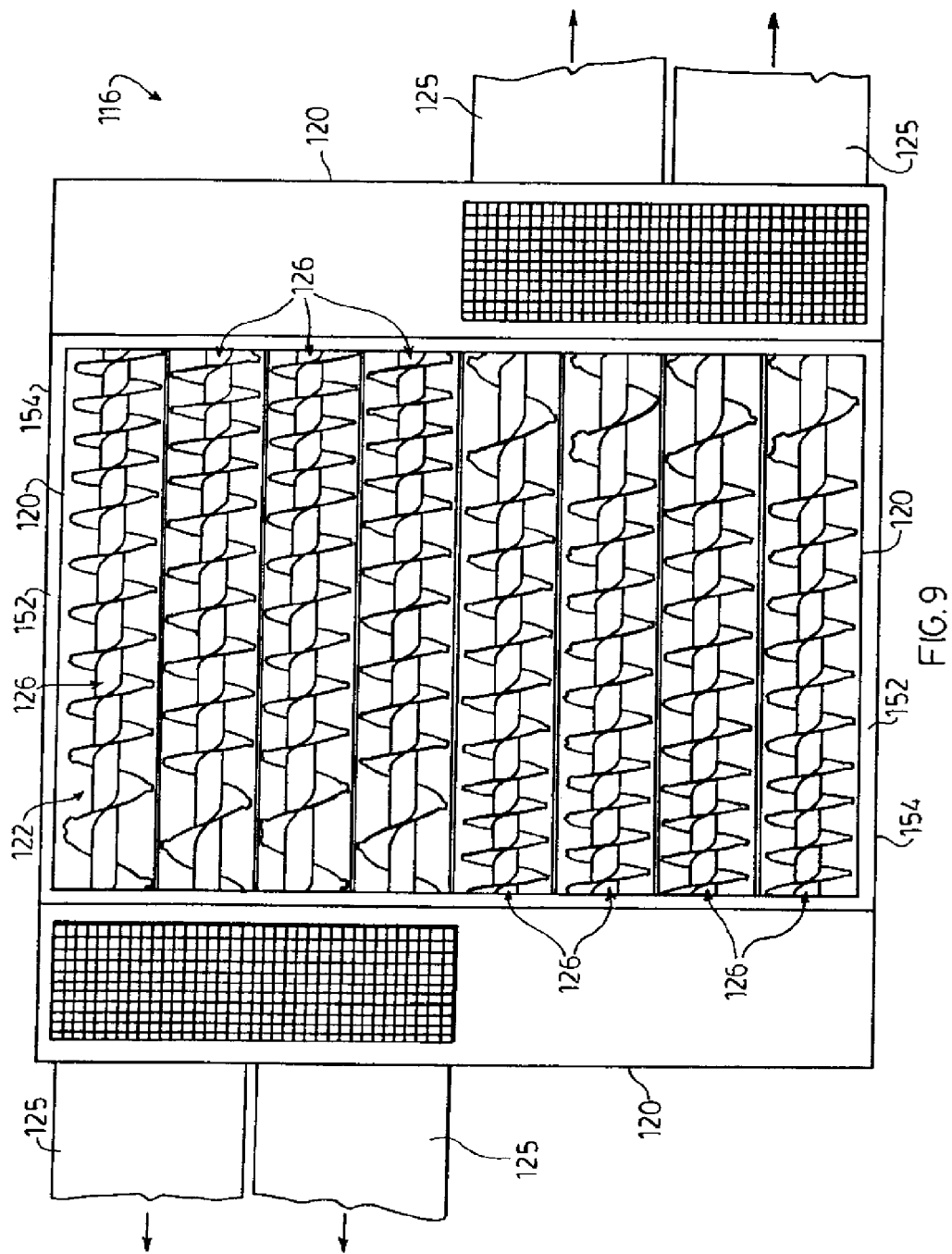
FIG. 9 is a top view of an alternate embodiment of a discharge member of the present invention; and, FIG. 10 is a cross-section taken along line 10-10 in FIG. 1.

It will be appreciated that in alternate embodiments, one or more screw conveyors 126 may be otherwise configured. For example, discharge member 116 may comprise only one screw conveyor 126 and one outlet 124, or discharge member 116 may comprise a plurality of screw conveyors which are not arranged in pairs, or discharge member 116 may comprise more than two pairs of screw conveyors. For example, in an alternate embodiment shown in FIG. 9, discharge member 116 comprises four discharge member outlets 124, and four pairs 132 of screw conveyors 126.

Referring to FIGS. 5 and 10, holding tank 100 preferably further comprises a heating jacket 136 provided on at least a portion of the sidewalls 102. For example, in the embodiment shown, heating jacket 136 surrounds all of each sidewall 102. Heating jacket 136 comprises a plurality of outer walls 140 that are generally parallel to and spaced from sidewalls 102 so as to define an enclosure 142 therebetween. A fluid may be passed through enclosure 142 from an inlet (not shown) to an outlet (not shown) so that a heated fluid is through enclosure 142. Heating jacket 136 may be of any construction known in the art. Accordingly, the cellulosic material may be heated to a desired temperature, or maintained at a desired temperature as it passes through holding tank 100.

Referring to FIG. 5, in a further preferred embodiment, discharge member 116 also comprises a heating jacket 146 provided on sidewalls 120 and/or base 118 of discharge member 116. Heating jacket 146 may be configured similarly to heating jacket 136, and may comprise an outer wall 154 spaced outwardly from sidewalls 120 and/or base 118 and is configured for passing a heated fluid through an enclosure 150 defined between outer walls 154 and sidewalls 120 and/or base 118.

A method of treating a cellulosic feedstock for ethanol production will now be described. Although the method will be described with reference to holding tank 100, it will be appreciated that the method may be carried out using an alternate apparatus, and holding tank 100 may be operated according to an alternate method.

A suitable cellulosic feedstock is preferably first treated to moisture impregnation to raise the moisture content of the feedstock to a predetermined level. Preferably, the moisture content of the feedstock upon entry to the holding tank is from about 30 wt % to about 60 wt %, preferably from about 45 wt % to about 55 wt %. This may be achieved by passing the feedstock through an impregnation chamber to an outlet of the impregnation chamber. The impregnation chamber may be, for example, impregnation chamber 10, and may comprise one or more conveyance members for urging the cellulosic feedstock along the impregnation chamber towards outlet 18 of impregnation chamber. As the cellulosic feedstock is passed through the impregnation chamber, it may be pre-treated by one or more of moistening the cellulosic feedstock and heating the cellulosic feedstock, as described in U.S. Publication Number 20100028089 A1, the disclosure of which is incorporated herein by reference in its entirety.

The cellulosic feedstock with or without being subjected to impregnation, is then conveyed to a holding tank wherein the feedstock is conveyed downwardly and laterally as it travels through the holding tank. For example, referring to holding tank 100, inlet 110 is disposed at an elevation above outlet 112. Accordingly, the material may migrate downwardly from the inlet towards the outlet under the force of gravity. Furthermore, as lower portion 108 has a greater cross sectional area than upper portion 106, the material will migrate laterally as it migrates downwardly.

Preferably, the method further comprises laterally conveying the cellulosic feedstock from the passage through the holding tank. Accordingly, once the feedstock reaches the exit of the holding tank, the feedstock is conveyed laterally to, e.g., one or more conduits in flow communication with a downstream process unit. For example, the holding tank may comprise a discharge member, such as discharge member 116, adjacent lower end 108. One or more screw conveyors 126 of the discharge member may convey the cellulosic feedstock laterally across outlet 112, as described hereinabove.

Alternately, or in addition, the cellulosic material is preferably actively withdrawn from essentially the entirety of outlet 112. The feedstock is therefore moved at least with an assistance of machinery out of the holding tank. For example, discharge member 116 may comprise a plurality of screw conveyors extending across outlet 112, which, when rotated, engage the cellulosic material adjacent the entirety of the outlet 112, and convey it towards a discharge member outlet, as described hereinabove.

In any embodiment, generally equally amounts of the cellulosic material is preferably withdrawn from each portion of the outlet 112. For example, a screw conveyor 126 of a discharge member 116 may have a helical flighting having a first pitch adjacent a discharge member outlet, and second pitch narrower than the first pitch distal to the discharge member outlet. Accordingly a generally equal amount of feedstock is withdrawn from the region adjacent a discharge member outlet, and from a region distal to a discharge member outlet.

In some embodiments, a first portion of the cellulosic feedstock is preferably withdrawn in a first lateral direction and a second portion of the cellulosic feedstock withdrawing a second portion of the cellulosic feedstock is preferably in a second lateral direction, which is preferably opposite to the first direction. For example, the holding tank may comprise a discharge member having a first pair of screw conveyors and a second pair of screw conveyors. Each screw conveyor may comprise a right-handed helical flighting, and the first pair of screw conveyors may be rotated in a first direction to convey the cellulosic feedstock in a first lateral direction, and the second pair of screw conveyors may be rotated in a second direction to convey the cellulosic feedstock in a second lateral direction.

In some embodiments, the method preferably further comprises maintaining a temperature in the passage of the holding tank between about 50° C. and about 75° C. For example, the holding tank may be provided with a heating jacket, such as heating jacket 136. The heating jacket may serve to heat the walls of the holding tank, such that the material within the holding tank is maintained at or raised to a temperature between 50° C. and about 75° C.

The method preferably comprises operating the holding tank such that the cellulosic feedstock moves from the inlet to the outlet in about 10 to 30 minutes. Accordingly, in use, the method may be preceded by an initial start up phase, wherein a discharge member of the holding tank is not operated, and the tank is filled with cellulosic feedstock from impregnation chamber 12. When the tank is filled, the method may commence, such that the holding tank is operated at steady state with a predetermined residence time.

It will be appreciated that certain features of the invention, which are, for clarity, described in the context of separate embodiments or separate aspects, may also be provided in combination in a single embodiment. Conversely, various features of the invention, which are, for brevity, described in the context of a single embodiment or aspect, may also be provided separately or in any suitable sub-combination.

Although the invention has been described in conjunction with specific embodiments thereof, if is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

We claim:

1. A method of preparing a cellulosic feedstock for ethanol production, comprising:
    passing the cellulosic feedstock through a moisture impregnation chamber to an outlet of the impregnation chamber, wherein the moisture content of the cellulosic feedstock is raised to from about 30 wt % to about 60 wt % and the temperature is raised to between about 50° Celsius and about 75° Celsius;
    passing the cellulosic feedstock from the outlet of the impregnation chamber to an inlet of a holding tank, the holding tank having an outlet, an upper portion, a lower portion and outer periphery extending between the inlet and the outlet of the holding tank, the lower portion having a greater cross-sectional area than the upper portion;
    conveying the cellulosic feedstock downwardly and laterally outwardly through the holding tank; and,
    withdrawing the cellulosic feedstock from the outlet of the holding tank.

2. The method of claim 1, further comprising maintaining a temperature in the holding tank between about 50° Celsius and about 75° Celsius.

3. The method of claim 2, wherein the cellulosic feedstock moves from the inlet to the outlet of the holding tank in about 10 to about 30 minutes.

4. The method of claim 1, wherein the inlet of the holding tank is disposed at an elevation above the outlet of the holding tank, and the cellulosic feedstock migrates from the inlet towards the outlet of the holding tank under the force of gravity.

5. The method of claim 1, further comprising conveying the cellulosic feedstock laterally across the outlet of the holding tank.

6. The method of claim 5, wherein the step of conveying the cellulosic feedstock laterally across the outlet of the holding tank comprises actively withdrawing the cellulosic feedstock from essentially an entirety of the outlet.

7. The method of claim 5, wherein the step of conveying the cellulosic feedstock laterally across the outlet of the holding tank comprises withdrawing a generally equal amount of cellulosic feedstock from each portion of the outlet.

8. The method of claim 5, wherein the step of conveying the cellulosic feedstock laterally across the outlet of the holding tank comprises withdrawing a first portion of the cellulosic feedstock in a first lateral direction and withdrawing a second portion of the cellulosic feedstock in a second lateral direction.

9. The method of claim 1, further comprising conveying the cellulosic feedstock from the outlet of the holding tank to a hydrolysis reactor downstream of the holding tank.

* * * * *